United States Patent [19]

Buchin

[11] Patent Number: 5,475,420
[45] Date of Patent: Dec. 12, 1995

[54] VIDEO IMAGING SYSTEM WITH IMAGE PROCESSING OPTIMIZED FOR SMALL-DIAMETER ENDOSCOPES

[75] Inventor: Michael P. Buchin, Palo Alto, Calif.

[73] Assignee: Origin Medsystems, Inc., Menlo Park, Calif.

[21] Appl. No.: 134,580

[22] Filed: Oct. 8, 1993

Related U.S. Application Data

[63] Continuation-in-part of Ser. No. 74,110, Jun. 9, 1993, abandoned.

[51] Int. Cl.$^6$ ........................................... H04N 5/21
[52] U.S. Cl. ........................ 348/72; 348/71; 348/65; 348/69; 348/67
[58] Field of Search ........................... 348/72, 71, 69, 348/67, 65; 128/6, 5, 7

[56] References Cited

U.S. PATENT DOCUMENTS

| | | | |
|---|---|---|---|
| 4,571,619 | 2/1986 | Mewitz | 358/160 |
| 5,088,492 | 2/1992 | Takayama et al. | 348/71 |
| 5,091,779 | 2/1992 | Ams et al. | 348/72 |
| 5,194,941 | 3/1993 | Grimaldi et al. | 358/22 |
| 5,196,928 | 3/1993 | Karasawa | 358/98 |
| 5,209,220 | 5/1993 | Hiyama et al. | 128/6 |
| 5,209,230 | 5/1993 | Hiyama et al. | 348/71 |
| 5,213,092 | 5/1993 | Uram | 128/4 |
| 5,257,100 | 10/1993 | Hattori et al. | 358/98 |
| 5,278,656 | 1/1994 | Hynecek et al. | 348/71 |
| 5,282,030 | 1/1994 | Nishimura | 348/72 |
| 5,305,098 | 4/1994 | Matsunaka et al. | 348/71 |
| 5,313,306 | 5/1994 | Kuban et al. | 348/71 |
| 5,347,987 | 9/1994 | Feldstein | 348/71 |

*Primary Examiner*—Tommy P. Chin
*Assistant Examiner*—Anand Rao
*Attorney, Agent, or Firm*—Limbach & Limbach

[57] ABSTRACT

An output video signal is derived from an input video signal generated by an image sensor in response to an image formed on only part of the image sensor. The output video signal is derived in response to only the portion of the input video signal generated by the part of the image sensor on which the image is formed. The input video signal additionally includes a portion generated by the part of the image sensor on which the image is not formed. An image signal generating apparatus is provided in which the image sensor is mounted, and which includes a detachably-attached image-forming device. When attached to the image signal generating apparatus, the image-forming device forms the image on the part of the image sensor. A frame of the input video signal is received from the image sensor. The frame of the input video signal has a structure and includes an image portion generated by the part of the image sensor on which the image is formed, and an external portion generated by the part of the image sensor on which the image is not formed. The image portion of the frame of the input video signal is identified, and the identified image portion is extracted from the frame of the input video signal to provide the image portion of a frame of the output signal which has a frame structure substantially similar to the frame structure of the input video signal.

45 Claims, 8 Drawing Sheets

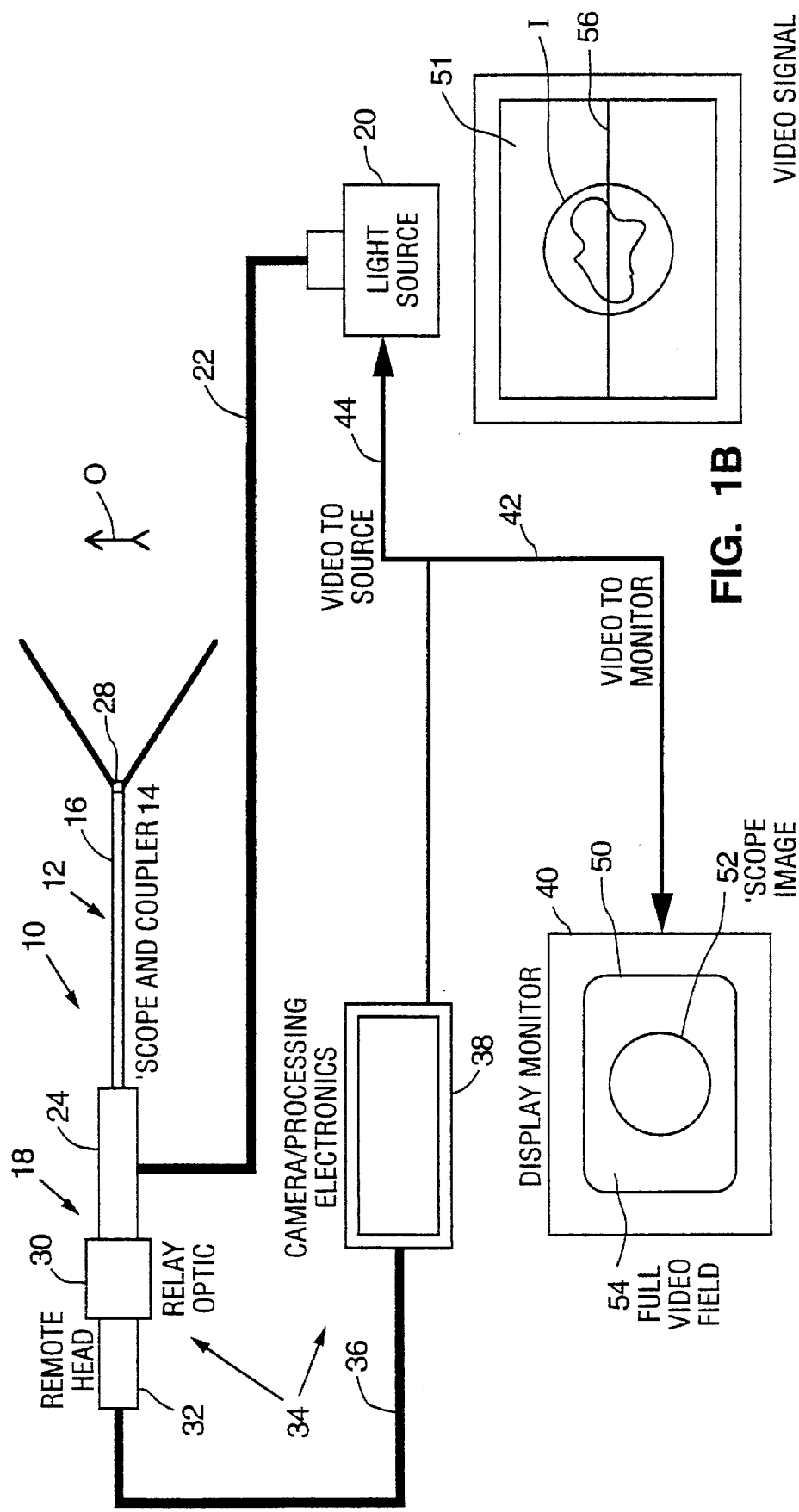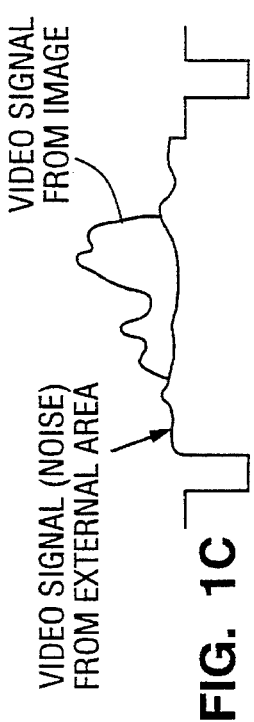

VIDEO IMAGING SYSTEM WITH IMAGE PROCESSING OPTIMIZED FOR SMALL-DIAMETER ENDOSCOPES

PRIOR APPLICATION

This application is a Continuation-in-Part of application Ser. No. 08/074,110 now abandoned, of inventor Michael P. Buchin, filed 9 Jun. 1993.

FIELD OF THE INVENTION

The invention relates to a method and apparatus for processing a video signal generated by an image sensor on which an image that occupies less than the total area of the sensor has been formed by a small-diameter endoscope.

BACKGROUND OF THE INVENTION

In fibre-optic endoscopes used in laparoscopy, a lens focuses an image of the object on the distal ends of a coherent bundle of optical imaging fibres. The image formed at the proximal end of the optical imaging fibres can be formed by a suitable lens into a real image for direct viewing, or can be focussed onto the image sensor of a video camera. The imaging bundle is surrounded by a layer of illuminating fibres through which light from a suitable high-intensity source is conducted to the distal end of the endoscope to illuminate the object.

Known video-based fibre-optic imaging systems are usually assembled from standard, commercially-available components: the image from the imaging bundle is focussed on the image sensor of a color video camera, and the resulting video signal is displayed on a commercial color video monitor. The illuminating fibres are normally illuminated with light generated by a 300-Watt Xenon-arc a 150–300-Watt metal halide light source, or some other suitable light source. Video cameras used in known video-based imaging systems use systems developed for the consumer and industrial video markets to control parameters affecting image quality. The average luminance level of the video signal is controlled by an automatic shutter that examines the whole of each frame of the video signal and electronically adjusts the amount of light collected by the image sensor by altering the integration time of the sensor. White balance (color mix and balance) is determined for the whole frame, and is electronically corrected.

Some known high-intensity light sources include a servo-controlled shuttering system that changes the intensity of the light illuminating the illuminating fibres to control the average luminance level of the video signal generated by the camera. The servo systems in such light sources operate in response to the average luminance level of each frame of the video signal generated by the camera. The video signal generated by the camera is connected to a servo input on the light source; the average luminance level of this signal is proportional to the average light level impinging upon the whole of the image sensor in the camera. A motorized shutter screen operates in response to the video signal from the camera to change the intensity of the light illuminating the illuminating fibres so as to maintain the average luminance level of the video signal substantially constant. However, many current video-based fibre-optic imaging systems rely upon the electronic shutter in the camera to set the luminance level of the video signal generated by the camera, and the current trend is towards increasing use of this technique.

Most currently-available video-based fibre-optic imaging systems are optimized for large-diameter endoscopes having an outside diameter in the range of 5 to 10 mm (0.2" to 0.4") and using standard rod lens assemblies. Endoscopes having a considerably smaller outside diameter in the range of 1 to 2 mm (0.04" to 0.08") using Gradient Index (GRIN) lenses and fibre-optic imaging bundles have been developed and are also available for surgical applications. Such endoscopes are advantageous in that they further reduce the size of incision required to insert them into a body cavity.

While some known video imaging systems are capable of generating images from small diameter endoscopes, they are typically restricted to use at short working distances, typically less than 2" (50 mm). If the image from the fibre-optic assembly is formed on the image sensor in the camera so that the image covers the whole area of the sensor, the resulting video picture of an object at an extended working distance has insufficient intensity when normal levels of illumination are used. Moreover, the video picture of an object at any working distance is pixellated, i.e., the picture clearly shows the outlines of the individual optical fibres of the imaging bundle and the voids around them, if present. These shortcomings are a result of the small diameter of the imaging bundle, and the relatively few (typically 1,600 to 25,000) optical fibres in the imaging bundle of a small-diameter endoscope.

A more acceptable video picture is obtained by reducing the size of the image of the imaging bundle formed on the image sensor in the camera so that the image occupies a fraction of the area of the sensor. This arrangement produces a video frame in which a central image of the imaging bundle is surrounded by a blank external area, and results in a video picture in which the intensity of the image is increased and the pixellation of the image is reduced. However, this arrangement also has some disadvantages. The pixels of the image sensor in the external area surrounding the image generate noise, especially when the light level of the image is low. This noise is visible in the blank external area of the frame, and can be distracting to the observer.

Also, the video signal generated in response to a frame in which a central image is surrounded by an external blank area causes the above-mentioned image quality control systems in known imaging systems to operate non-optimally. For example, the control signal in the camera or the light source that controls the average luminance level of the video signal generated by the camera is derived in response to each complete frame of the video signal. A change in the intensity of an image occupying a fraction of the frame produces a smaller change in the control signal than a similar change in the intensity of an image filling the whole of the frame. As a result, the intensity control system cannot maintain the image part of the video picture at a substantially constant intensity. As a side effect of this, luminance saturation in the image can occur.

As another example, none of the image of the imaging bundle extends beyond the frame of the video picture. Consequently, any non-uniform illumination of the object, or varying radial sensitivity of the imaging bundle will be visible in the displayed image.

Small-diameter fiber-optic endoscopes present additional problems when used in large body cavities. In such applications, endoscopes with a hyper-extended working distance, greater than 50 mm (2) are used. Since the light reaching the image sensor is inversely related to the fourth power of the working distance, to provide the light level required to produce a satisfactory video image, a very high light intensity is required. With such a high light intensity, the distal tip of the endoscope can overheat if it comes into contact with tissue or objects.

Known camera-based or light source-based average luminance level control systems suffer from an additional operational problem as a result of their being responsive to the whole of the video frame. High intensity light reflected from highly reflective objects, such as metal instruments, fluid pools, etc., in the field of view can cause the control system to maintain the set average luminance level by reducing the luminance level of the whole of the frame. This can cause the part of the frame being observed by the surgeon to disappear into black level. Time must then be wasted repositioning the reflective object and/or the endoscope, or adjusting the video system, to restore the visibility of the part of the frame being observed.

It is known in consumer video systems to derive a signal for operating an auto focus system from an small area, normally in the center, of the image sensor in the camera. It is also known in endoscopic video systems to derive a signal for adjusting white balance from a small area, normally in the center, of the image sensor in the camera. In both of these known systems, however, the relationship between the small area and the image is undefined.

OBJECTS AND SUMMARY OF THE INVENTION

It is an object of the present invention to provide a video-based fibre-optic imaging system in which an image of the imaging bundle is formed on on less than the total area of the image sensor, and in which a small-diameter endoscope is automatically detected, and the video processing required as a result of the image being formed on less than the total area of the image sensor is automatically selected in response to such detection.

It is an object of the present invention to provide a video-based fibre-optic imaging system in which an image of the imaging bundle is formed on less than the total area of the image sensor, and in which parameters relating to the video picture are detected according to the type of endoscope connected to the system.

It is an object of the present invention to provide a video-based fibre-optic imaging system in which an image of the imaging bundle is formed on less than the total area of the image sensor, and in which the luminance level with which the image is displayed is controlled by the luminance of the image, and not by the average luminance of the whole video frame.

It is an object of the present invention to provide a video-based fibre-optic imaging system in which an image of the imaging bundle is formed on less than the total area of the image sensor, and in which a signal is provided for controlling the imensity of the light source to provide an image luminance that is determined by the luminance of the image.

It is an object of the present invention to provide a video-based fibre-optic imaging system in which an image of the imaging bundle is formed on less than the total area of the image sensor, and in which a signal is provided for controlling the automatic shutter system in the camera to provide an image luminance that is determined by the luminance of the image.

It is an object of the present invention to provide a video-based fibre-optic imaging system in which an image of the imaging bundle is formed on less than the total area of the image sensor, and in which the intensity of the light source is significantly reduced when the tip of the fibre-optic assembly touches tissue or an object to avoid tip heating.

It is an object of the present invention to provide a video-based fibre-optic imaging system in which an image of the imaging bundle is formed on less than the total area of the image sensor, and in which the luminance level of the image is unaffected by light reflected from highly-reflective small objects in the frame.

It is an object of the present invention to provide a video-based fibre-optic imaging system in which an image of the imaging bundle is formed on less than the total area of the image sensor, and in which spatial intensity variations in the image can be corrected.

It is an object of the present invention to provide a video-based fibre-optic imaging system in which an image of the imaging bundle is formed on less than the total area of the image sensor, and in which the noise level in low-level parts of the image is reduced.

Accordingly, the invention provides a method for deriving an output signal from an input video signal generated by an image sensor having an image formed on a part thereof. The input video signal includes an image portion generated by the part of the image sensor on which the image is formed, and an external portion generated by the part of the image sensor on which the image is not formed. In the method according to the invention, the image portion of the input video signal generated by the part of the image sensor on which the image is formed is identified, and the identified image portion of the input video signal is processed to provide the output signal.

When the image is formed on part of the image sensor by one of plural types of image-forming apparatus, the type of image-forming apparatus forming the image is determined, and the image portion of the input video signal is identified in response to the determined type of image-forming apparatus.

When only one type of image-forming apparatus forms the image on part of the image sensor, it is determined when the one type of image-forming apparatus is forming the image on part of the image sensor, and the external portion of the input video signal is identified in response to the determination that the one type of image-forming apparatus is forming the image on part of the image sensor.

When the image is formed on part of the image sensor by an image-forming apparatus that has stored in it image information for the image-forming apparatus, the stored image information for the image-forming apparatus is retrieved from the image forming apparatus, and the external portion of the input video signal is identified using the retrieved stored image information. Image information is information identifying the external portion of the input video signal generated by the part of the image sensor on which the image is not formed by the image-forming apparatus.

The external portion of the input video signal may alternatively be identified by determining the lines of the input video signal that include an image part generated by the part of the image sensor on which the image is formed, and an external part generated by the part of the image sensor on which the image is not formed. Then, for each line so identified, the position of the boundary between the image part and the external part is determined.

When the image formed on part of the sensor has a known shape, but an unknown position on the image sensor, and an unknown size, the external portion of the input video signal may be identified by analyzing the input video signal to determine parameters for calculating the size and the position of the image on the image sensor. Then, the boundary lines having an image portion and an external portion are calculated from the determined parameters and the known shape of the image. Finally, for each boundary line, the position of the boundary between the image part and the external part is calculated.

The method according to the invention applies a position-dependent correction to the image portion of the input video signal as follows: the image includes plural image elements that each have a position in the image, and the image portion of the input video signal includes plural signal elements, that each correspond to an image element. In the step of processing the image portion, an element of the input signal is multiplied by a position-dependent function that depends on the position in the image of the image element corresponding to the signal element.

The method according to the invention provides the output signal as a control signal for controlling an automatic luminance system responsive to the average level of a control signal by deriving from a frame of the input video signal a portion of the output signal having an average level corresponding to the average luminance of the image portion of the frame of the input video signal.

The output signal may be a control signal, or a video signal for use by the automatic luminance system as a control signal. The automatic luminance system may be camera-based or light-source based.

The method according to the invention can provide an output signal that is a video signal with an image portion with a lower noise level than the image portion of the input video signal as follows: corresponding parts of successive frames of the image portion of the input video signal are stored in corresponding memory locations in successive pages of a memory. The corresponding parts stored in corresponding memory locations in the successive pages of the memory are averaged to provide average values. Finally, the output signal having a image portion derived from the average values is provided.

Alternatively, an accumulated sample value for an element of the image portion of the input video signal can be read from a storage location in a memory. The stored accumulated sample value is multiplied by a degradation factor to provide a multiplied accumulated sample value. The multiplied accumulated sample value and a sample value of an element of the image portion of the input video signal corresponding to the multiplied accumulated sample value are averaged to provide an average value. The average value is provided as the sample value of the element of the image portion of the output signal corresponding to the element of the input signal. Finally, the average value is stored in the storage location in the memory as the accumulated sample value.

The invention also provides an apparatus for deriving an output signal from an input video signal generated by an image sensor having an image formed on a part of it. The input video signal includes an image portion generated by the part of the image sensor on which the image is formed, and an external portion generated by the part of the image sensor on which the image is not formed. The apparatus comprises a frame store memory for storing either the input video signal of the output signal and a digital signal processor that operates together with the frame store memory. The digital signal processor is programmed to identify the image portion of the input video signal generated by the part of the image sensor on which the image is formed, and to process the identified image portion of the input video signal to provide the output signal.

BRIEF DESCRIPTION OF THE DRAWINGS

FIG. 1A shows a block diagram of a known video-based fibre-optic imaging system.

FIG. 1B shows an image of the proximal end of the imaging bundle formed on a part of the area of the image sensor in a known video-based fibre-optic imaging system.

FIG. 1C shows one line of the video signal generated from the image sensor shown in FIG. 1B.

DETAILED DESCRIPTION OF THE INVENTION

Figure 2:
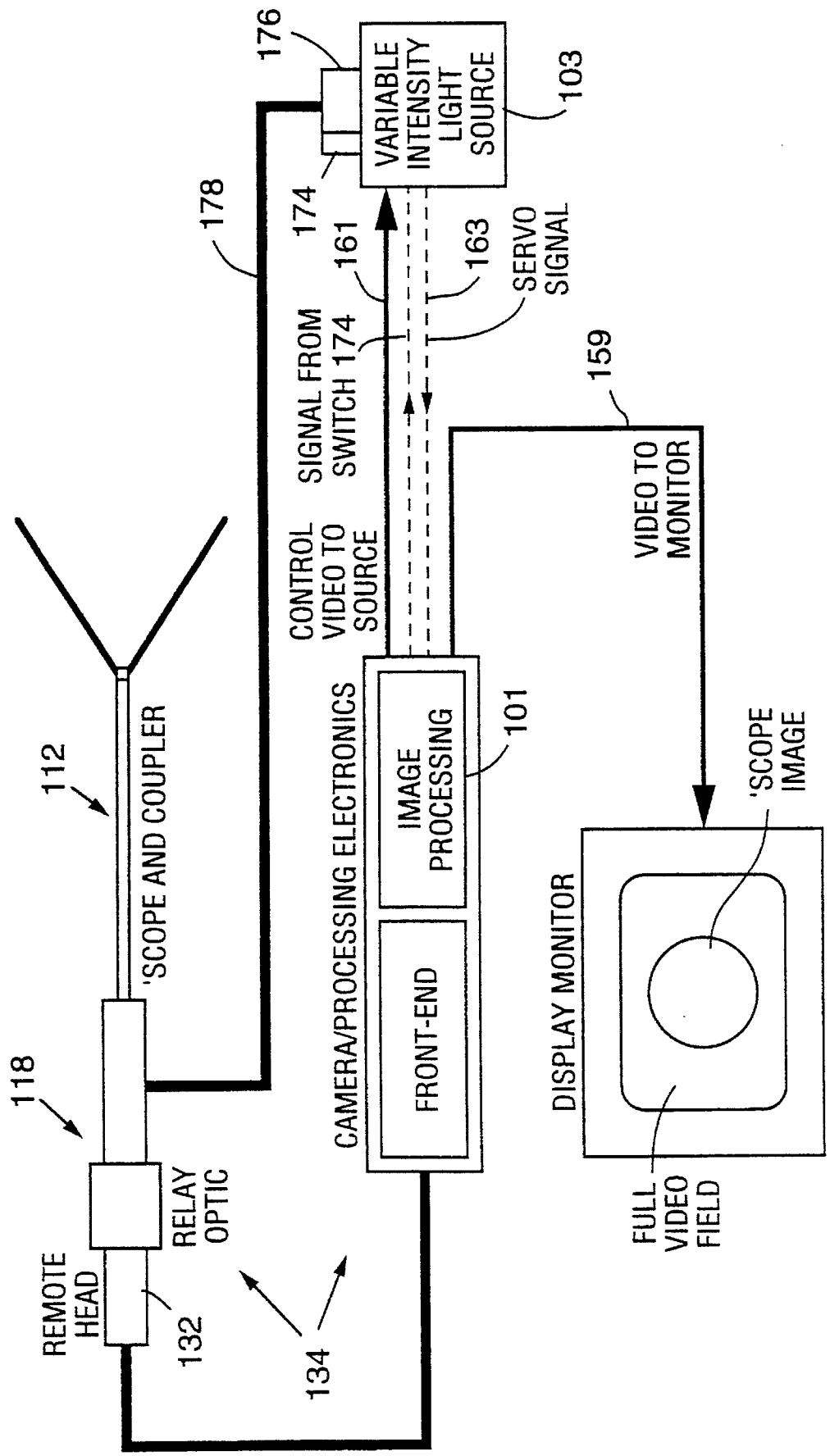
FIG. 2 shows a block diagram of a video-based fibre-optic imaging system according to the invention.

FIG. 1A shows a block diagram of a known video-based fibre-optic imaging system for use with an endoscope, or other optical instruments. In FIG. 1A, the endoscope 10 includes the fibre-optic assembly 12, a coaxial or parallel arrangement of the inner imaging fibre-optic bundle 14 and the outer illuminating fibres 16. The imaging bundle normally includes between 1,600 and 25,000 optical fibres.

The fibre-optic assembly 12 is detachably attached to the optical assembly 18. This allows a common optical assembly 18 to be used with fibre-optic assemblies optimized for different working distances, and also allows disposable fibre-optic assemblies to be used.

The optical assembly 18 couples light transmitted from the light source 20 through the fibre-optic bundle 22 and the coupler 24 into the illuminating fibres 16. Light emitted from the distal end of the illuminating fibres illuminates the object O. Light from the object O is gathered by the lens 28 on the distal tip of the imaging bundle 14, and transmitted through the imaging bundle into the optical assembly 18. The object O may well be situated at an extended working distance from the distal tip of the endoscope 10. However, the invention is equally applicable to endoscopes used at non-extended working distances.

The optical assembly 18 also includes the relay optic 30, which forms a real image of the proximal ends of the optical fibres of the imaging bundle 16, including the transmitted image of the object O, on the remote head 32 of the video camera 34. The remote head 32 includes an image sensor, which is a preferably charge-coupled device (CCD) array with color filters formed on the sensor surface. The remote head also includes the drive circuitry and video amplifier for the CCD array. A 784×492-element CCD array with 385,728 pixels is used in the preferred embodiment, and will be referred to in the various examples to be described below. CCD arrays with alternative pixel arrangements can equally be well used. Plural CCD arrays with color filters, or a CCD array without color filters can also be used.

The cable 36 connects synchronizing pulses from the camera electronics 38 to the remote head 32, and connects the video output of the remote head to the camera electronics. This video output could be an analog video signal, with or without synchronizing pulses, or could be a digital bit stream representing a video signal, or could be pixel data. The camera electronics derive a normal NTSC composite video signal or a component video signal from the video output from the remote head.

The camera electronics normally include circuitry for automatically adjusting the whim balance of the video signal, and normally also include an automatic shutter circuit and an automatic gain control. The automatic shutter circuit varies the integration time of the CCD array to keep the luminance level of the video signal generated by the remote head within a predetermined range.

The video signal 42 from the camera electronics 38 is fed to the video monitor 40. The camera electronics may also feed the video signal via the path 44 to the light source 20 to provide a feedback signal thereto, in which case, the automatic shutter and gain controls in the camera are preferably defeated. The feedback signal is used by a servo that controls a motorized shutter varying the light output of the light source 20 to keep the luminance level of the video signal within a predetermined range. However, most systems currently in use rely on an electronic shutter circuit in the camera to maintain the luminance level of the video signal 42.

When the fibre-optic assembly 12 has a small diameter, e.g., an outside diameter of less than 2 mm, the optical assembly 18 forms an image I of the proximal end of the imaging bundle 14 on only part of the area of the CCD array 51 in the remote head 32, as shown in FIG. 1B. This is done to provide an adequate light level on the part of the CCD array on which the image is formed, and hence image brightness, and to avoid obvious pixellation, as described above. One typical line of the resulting video signal is shown in FIG. 1C.

The resulting video picture is shown on the monitor 40 in FIG. 1A. Only part of the frame 50 is occupied by the image 52 of the proximal end of the imaging bundle 14. The external area of the video frame surrounding the image is nominally blank, but includes noise generated by the unilluminated pixels of the CCD array, as shown in FIG. 1C. The noise is especially severe when the light level falling on the pixels of the CCD array on which the image is formed is low, and the automatic shutter control in the camera increases the integration time to provide the predetermined video signal level.

Noise reduces the apparent quality and contrast of the image, and is distracting to the observer. In known systems operating at hyper-extended working distances, the light level on the pixels of the CCD array on which the image is formed tends to be low. The illumination of an object falls off in proportion to the square of the distance of the object from the distal end of the illuminating fibres, and the light returning to the imaging fibres also falls off in proportion to the square of the distance of the distance between the distance of the object from the distal end of the endoscope. In other words, the light level on the pixels of the CCD array falls off in proportion to the fourth power of the distance of the object from the distal end of the endoscope. Moreover, in a conventional system using a camera-based automatic shutter system, the light level on the pixels of the CCD array cannot be increased by increasing the light intensity emitted by the illuminating fibres because of the possibility of overheating, and optical limitations of illumination technology.

In known systems, the efficacy of the camera-based automatic shutter system is considerably reduced when the video frame consists of a central image surrounded by a blank area. This is because such systems respond to the average brightness over the whole frame. It can be seen that, with so much of the screen blank, the level of the video signal generated by the image part of the video frame can change significantly and yet have a relatively small effect on the average level of the video signal over the whole frame.

Also, for the same reason, the efficacy of an automatic luminance level control that varies the output of the light source is also considerably reduced when the video frame consists of a central image surrounded by an external blank area.

FIG. 2 is a block diagram of a video-based fibre-optic imaging system according to the invention for use with an endoscope, or other optical instrument. The imaging system according to the invention can be used with endoscopes of all diameters, but is most advantageous when used with a small-diameter endoscope that forms an image on less than the full area of the image sensor in the camera. Components in the imaging system according to the invention that are the same as components of the known imaging system are indicated with the same reference number.

In the imaging system shown in FIG. 2, the video output forms the remote camera head 132 is processed by the image processing electronics 101. The image processing electronics automatically determine when the image is formed on less than the full area of the CCD array. In response to this determination, the image processing electronics process the part of the video signal generated in response to the external area differently from the part of the video signal generated in response to the image. The image processing electronics also control the automatic exposure system in response only to the pixels on which the image is formed. In controlling the automatic exposure system, the image processing electronics ignore reflections from small, bright objects such as instruments. The image processing electronics also apply a correction for non-uniform radial sensitivity or illumination of the image. Finally, the image processing electronics also apply signal averaging between consecutive frames of the video signal to reduce noise, at least at low luminance levels.

In the video imaging system shown in FIG. 2, the automatic shutter system in the camera 134 is preferably disabled, and the variable-intensity light source 103 which has a greater maximum intensity than the light source of a conventional system is included in the system. This improves the signal-to-noise ratio of the video images produced by the imaging system according to the invention compared with a conventional fibre-optic imaging system because the video imaging system according to the invention operates with a higher maximum illumination level than the conventional system.

The variable-intensity light source 103 is controlled by a control video signal 161 synthesized by the image processing electronics to provide automatic exposure control by varying the intensity of the variable-intensity light source 103 in response to the illumination level of the image only. The illumination level in the external area surrounding the image does not contribute to controlling the intensity control servo. Further, the control video signal is derived in a way that ignores reflections from small, bright objects to further improve the accuracy of the automatic exposure control.

The control video signal 161 is suitable for feeding into the video input of a conventional variable-intensity light source. Alternatively or additionally, the image processing electronics can generate the servo signal 163 that controls the intensity of the variable-intensity light source directly.

The illumination level can be increased, and a higher maximum light intensity can be used because controlling the intensity of the variable-intensity light source in response to the illumination level of the image only makes the light intensity control much more responsive to the illumination level of the image. Accordingly, the light intensity control can be relied upon to reduce the illumination level automatically as the distal end of the endoscope approaches an object or tissue. This automatically prevents the optical fibres from overheating if the endoscope tip touches the object or tissue.

Alternatively, a fixed-intensity light source can be used, and exposure control that is more accurate than that obtained using known techniques can be obtained by controlling the camera-based automatic exposure system by the control video signal 161 or the servo signal 163.

Figure 3A:
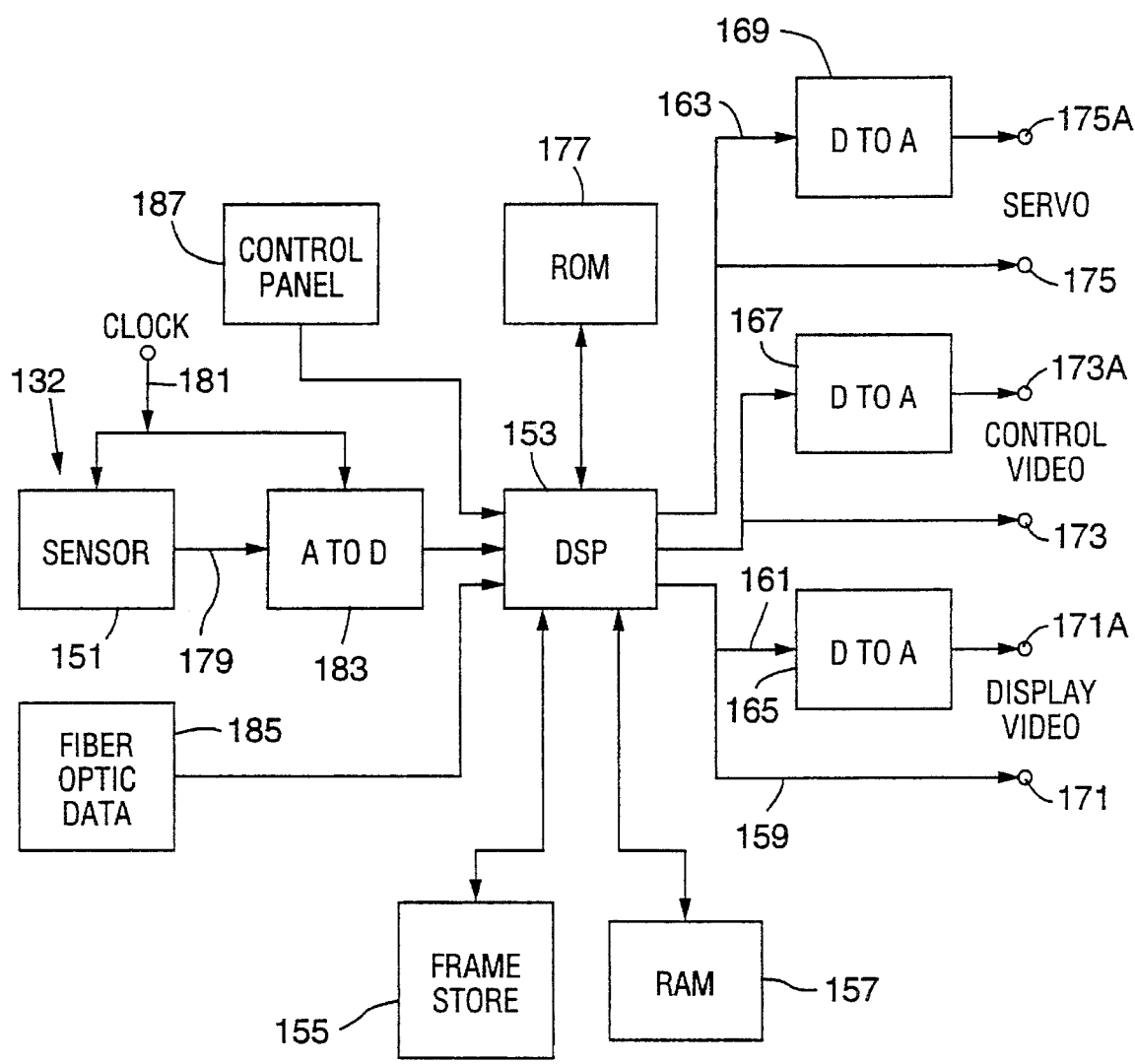
FIG. 3A shows a block diagram of the image processing electronics of a video-based fibre-optic imaging system according to the invention.

A block diagram of the preferred embodiment of the image processing electronics 103 is shown in FIG. 3A. The preferred embodiment digitizes the output of the image sensor CCD array 151 in the remote head 132, and uses the video digital signal processor (DSP) 153 and its associated memories 155 and 157 to carry out the image processing to be described below. The digital signal processor also encodes the image-processed digital video signal into a digital video output signal 159. In the following description, an embodiment producing an NTSC composite video signal as the digital video output signal will be described, but the principles described herein can readily be adapted to produce other format composite video signals, e.g., PAL, SECAM, component video signals, e.g., S-video, R,G,B or Y,I,Q component video, or high-definition video signals.

The digital signal processor 153 also synthesizes a digital control video signal 161 for feeding into the video input of the variable-intensity light source 103 (FIG. 2), and a digital servo signal 163 for alternatively controlling the variable-intensity light source directly.

The digital composite video signal 159, the digital control video signal 161, and the digital servo signal 163 are fed to the output terminals 171, 173, and 175, respectively, for connection to the parts of rest of the system that require a digital signal. The signals 159, 161, and 163 are also fed to the digital-to-analog converters 165, 167, and 169, respectively, where they are converted into analog signals, which are fed to the output terminals 171A, 173A, and 175A for connection to the parts of the rest of the system requiring an analog signal.

Alternatively, the image processing electronics can be provided using different arrangements of digital circuitry, or by analog processing.

The digital signal processor 153 executes a main routine that can call various routines to perform the different aspects of image processing. The routines are stored in the Read-only Memory 177 or in some other form of non-volatile memory. Working results and other data are stored in the Random Access Memory (RAM) 157.

The video output 179 of the CCD array 151, produced in response to the clock signal 181, is fed into the analog-to-digital converter 183, which converts the analog voltage generated by each pixel of the array into a sample, which is preferably an 8-bit binary number. The resulting samples are fed into the DSP 153, which stores the set of samples for one frame generated by one scan of the CCD array in the frame store memory 155. The samples are preferably stored in a matrix arrangement of memory elements corresponding to the lines and pixels of the CCD array so that the memory location in which the sample for an individual pixel is stored can be addressed using the line number and pixel number of the pixel.

The DSP 153 derives each frame of the digital video output signal 159 and the digital control video signal 161 by sequentially reading each pixel of the frame from the frame store 155, and applying appropriate processing.

Each of the various processing operations of the DSP 153 will now be described.

1. Image Boundary Detection

In this processing operation, the digital signal processor determines, in terms of lines and pixels, an image boundary table defining the area of the CCD array on which the image is formed. The image boundary table, which is stored in the RAM 157, is then used to process the data received from the image sensor 151.

In the following explanation, a pixel on which the edge of the image falls will be called a "boundary pixel." Each line that includes a boundary pixel will be called a "boundary line." Since the image is substantially symmetrical, each boundary line includes two boundary pixels, a left boundary pixel and a right boundary pixel. The boundary lines closest to the top of frame and to the bottom of the frame will be called the "top boundary line" and the "bottom boundary line," respectively.

Two main types of image boundary detection will be described. In the first main type, the DSP 153 simply retrieves stored image boundary parameters defining a boundary table or from which a boundary table can be calculated. In the second main type, the DSP executes a routine that determines the image boundary empirically. Image boundary parameters can be used as the sole means for determining the image boundary if close tolerances can be guaranteed in the optical system. If close tolerances cannot be guaranteed, and the size and position of the image on the image sensor can vary, a combination of image boundary parameters and empirical determination is preferably used to determine the image boundary. The image boundary parameters simplify and speed up the empirical determination algorithm.

In the first main type of boundary detection, the image boundary parameters may be stored in the image processing electronics 101, or in the fibre-optic assembly 112. Plural sets of parameters may be stored in the image processing electronics 101, and the appropriate set of parameters for the fibre-optic assembly being used may be automatically selected.

The image boundary parameters could be the actual values of the image boundary table, or could include information indicating the pixel numbers of the left and right boundary pixels (if any) for each line of the video frame, or information from which these pixel numbers can be determined. The information from which the pixel numbers of the boundary pixels on each line can be determined could be in the form of a table defining whether or not the image is formed on each pixel on each line of the frame, or a table defining the pixel number of the boundary pixels of each line. Alternatively, image boundary parameters such as those defining the shape of the image, the location of its center, and its size, could be inserted into an algorithm that calculates the boundary table.

The image boundary table could consist of a flag bit for each pixel of the CCD array 151. In response to the parameters retrieved from storage, the DSP 153 sets each flag bit in the flag section according to whether the image is formed on the pixel corresponding to the flag bit. Alternatively, the image boundary table could consist of a number pair for each line. The number pair consists of the two pixel numbers of the boundary pixels of each line. The number pair for each line which is not a boundary line would include a number outside the range of pixel numbers, e.g., a number greater than 783, to indicate that the line is not a boundary line.

Preferably, the image boundary table stores a number pair for each boundary line, plus an additional number pair. The additional number pair consists of the line numbers of the top and bottom boundary lines. The rest of the number pairs consist of a number pair for each boundary line between the top boundary line and the bottom boundary line, inclusive. The number pair consists of the pixel numbers of the left and right boundary pixels. The image boundary table stored in the RAM 157 is used by the DSP 153 in performing the image processing that will be described below.

(a) Stored Image Boundary Parameters

In this approach, a switching arrangement detects connection of a small-diameter fibre-optic assembly to the optical assembly. When a small-diameter fibre-optic assembly is detected, the digital signal processor retrieves the image boundary parameters from a memory.

i. Small-Diameter Fibre-Optic Assembly Detection

Figure 4A:
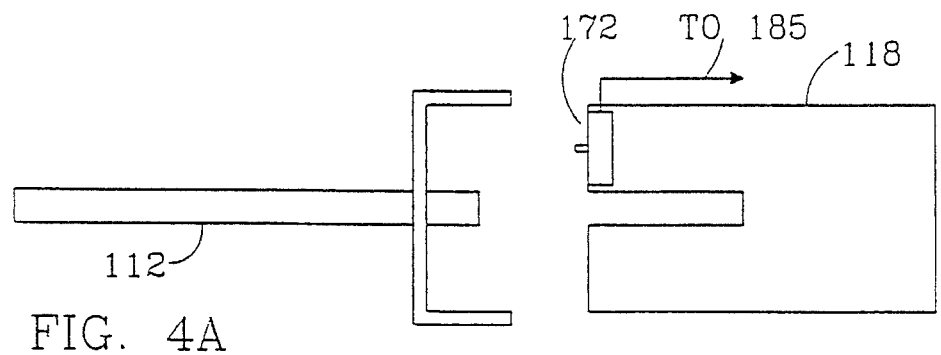
FIG. 4A shows an endoscope incorporating automatic switching for a small-diameter fibre-optic assembly according to the invention.

FIG. 4A shows the switch 172 built into the optical assembly 118. The switch 172 may be a mechanical or an LED switch, or some other suitable type of switch. The switch is activated when a small-diameter endoscope is attached to the optical assembly, but not when a normal-diameter fibre-optic assembly is attached to the optical assembly.

Alternatively, a shown in FIG. 2, the switch 174 may be built into the connector 176 in the variable intensity light source 103. Such light sources have plural connectors for different types of illuminating fibre cables. The connector 176 is for the illuminating fibre cable 178 of a small-diameter fibre-optic assembly. Thus, the switch 174 would be activated when the illuminating fibre cable 178 of a small-diameter fibre-optic assembly is plugged into the connector 176, but would not be activated when the illuminating cable assembly of a large-diameter fibre-optic assembly were plugged into a different connector on the light source 103.

The signal from the switch 172 or 174 is received by the fibre-optic data unit 185, which passes the signal to the DSP 153. In response to the signal, the DSP retrieves a set of image boundary parameters from a memory, such as the RAM 157 or the ROM 177, and begins processing data received from the image sensor 151 in response to the image boundary data. This arrangement works with an endoscope that can accept only a single type of small-diameter fibre-optic assembly. The image boundary data pertaining to this single type of fibre-optic assembly would be stored in the memory. Even if a different type of small-diameter fibre-optic assembly were used with his arrangement, the results, although inaccurate, may be better than having no image processing at all.

ii. Fibre-Optic Assembly Type Sensing

This arrangement provides accurate processing of the image with plural types of fibre-optic assembly. In this arrangement, shown in FIG. 4B, each type of fibre-optic assembly would be coded with a type identification number that identifies the type of the fibre-optic assembly. When the fibre-optic assembly is attached to the optical assembly, the type identification number would read out, and the DSP 153 would retrieve from a memory the image boundary data pertaining to the type of fibre-optic assembly identified by the time identification number. The DSP would then process the data from the sensor 151 according to the image boundary data. The type identification number could be stored using a simple arrangement, for example, holes in the fibre-optic assembly could operate mechanical or LED switches built into the optical assembly 118, or some other arrangement could be used.

Figure 4B:
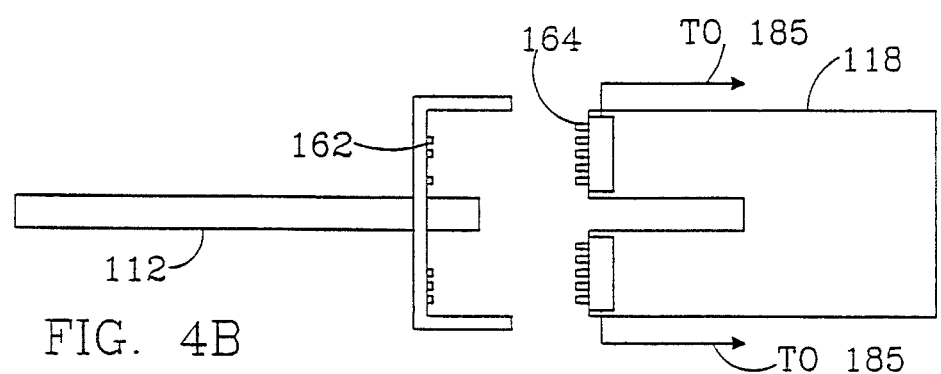
FIG. 4B shows an endoscope incorporating automatic type identification according to the invention.

FIG. 4B shows the fibre-optic assembly 112 having a coded arrangement of cams 162. The cams operate contacts in a bank of micro switches 164 built into the optical assembly 118. When the fibre-optic assembly is attached to the optical assembly, the cams change the state of certain ones of the micro switches. The outputs of the micro switches are fed into the fibre-optic data unit 185 as the type identification number of the fibre-optic assembly. Alternatively, the type identification number could be stored in a read-only memory built into the fibre-optic assembly. In an arrangement similar to that which will be described below, the fibre-optic data unit 185 would retrieve the type identification number from the read-only memory.

The fibre-optic data unit 185 transmits the type identification number of the fibre-optic assembly to the DSP 153, which looks up such parameters as the working distance, size, shape, f-number, orientation, number of fibres, radial non-linearity, and the image boundary parameters, etc. for the fibre-optic assembly in response to the type identification number. These parameters for a number of different types of fibre-optic assembly would be stored in a look-up table in the RAM 157, the read-only memory 177, or in some other memory.

iii. Data Retrieval from the Fibre-Optic Assembly

Figure 4C:
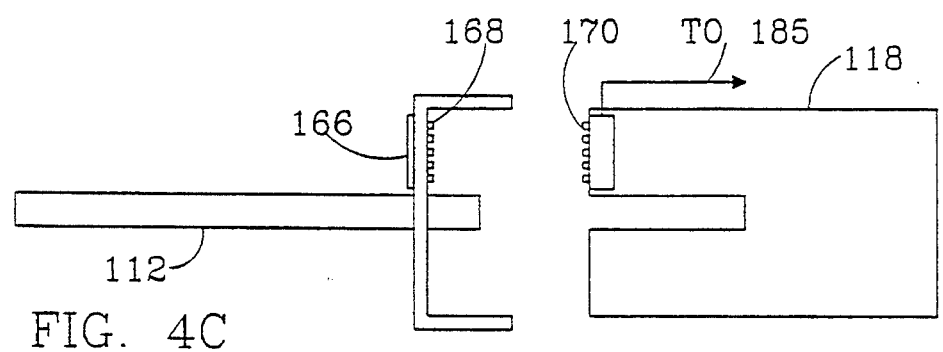
FIG. 4C shows an endoscope incorporating a memory from which image processing parameters can be retrieved according to the invention.

Instead of being coded with a type identification number, each fibre optic assembly could store data defining parameters such as the working distance, size, shape, f-number, orientation, number of fibres, radial non-linearity, image boundary parameters, etc. for the assembly. FIG. 4C shows an arrangement in which the parameters are stored in the read-only memory 166 built into the fibre-optic assembly. Opposing contacts 168 and 170 on the fibre-optic assembly 112 and the optical assembly 118 allow the DSP 153 to interrogate this memory via the fibre-optic data unit 185.

Any change in the data fed to the DSP 153 by the fibre-optic data unit 185 would cause the DSP execute a set-up routine. The image boundary parameters retrieved from the read-only memory 166 will indicate whether the image fills the sensor. If the image boundary parameters indicate that the image is formed on only a part of the sensor, image processing is required, and the DSP 153 will store the image boundary parameters and the other parameters in the RAM 157, and carry out image processing in response to them.

(b) Universal Image Boundary Detection

In this approach, the location of the boundary pixels on each line on which the image falls is determined by examining the digital video samples stored in the frame store 155. This approach allows any type of fiber-optic assembly to be used since it does not require a special fibre-optic assembly in which data is stored. This approach also enables variations and errors in the optical assembly 118 to be taken into account. The DSP 163 can execute the set-up routine shown in FIG. 5 when the system is switched on, or in response to the fibre-optic data unit 185 detecting that a fibre-optic assembly has been connected to the optical assembly 118. This requires a switch operated by connecting the fibre-optic assembly to the optical assembly, similar that shown in FIG. 4A. Alternatively, the DSP 153 can detect black level (or a low level) at several points near the perimeter of the sensor, indicating that the image is formed on less than the full area of the image sensor, and execute the set-up routine in response to this detection. During execution of the set-up routine, the optical assembly is pointed at a well-illuminated target.

It is preferred that the set-up routine be executed after the optical assembly has been focussed. Execution of the set-up routine can be triggered by the user operating an appropriate control on the control panel 187 after the optical assembly has been focussed. Alternatively, the set-up routine can be adapted to perform a rough determination of the location of the boundary pixels, and to monitor the sharpness of the boundary. Only after the set-up routine determines that the boundary has the degree of sharpness resulting from the optical assembly being properly focussed will the set-up routine perform a final, accurate determination of the location of the boundary pixels.

Since, with some optical systems, the image size changes when the focus is changed, the DSP 153 can be programmed to execute a check routine that checks whether the image boundary coincides with the image boundary determined by the set-up routine. For simplicity, the check routine can check a number of sample points on the image boundary instead of every point on the image boundary. The check routine could be executed in response to a determination that an auto-focus circuit has changed the focus. Alternatively, the check routine could be used to provide focusing data to control an auto-focus system.

If the check routine determines that the image boundary does not coincide with the image boundary determined by the set-up routine, the check routine causes the set-up routine to re-execute. The check routine also checks the illumination level at several points near the image boundary, and only instigates re-execution of the set-up routine when a boundary discrepancy is detected, and the illumination levels are determined to be high enough to ensure that the set-up routine will produce a reliable result. Alternatively, or additionally, the check routine could display a message on the monitor 40 indicating that the set-up routine was executinmg and prompting the user to direct the fibre-optic assembly towards a well-illuminated object.

Figure 5:
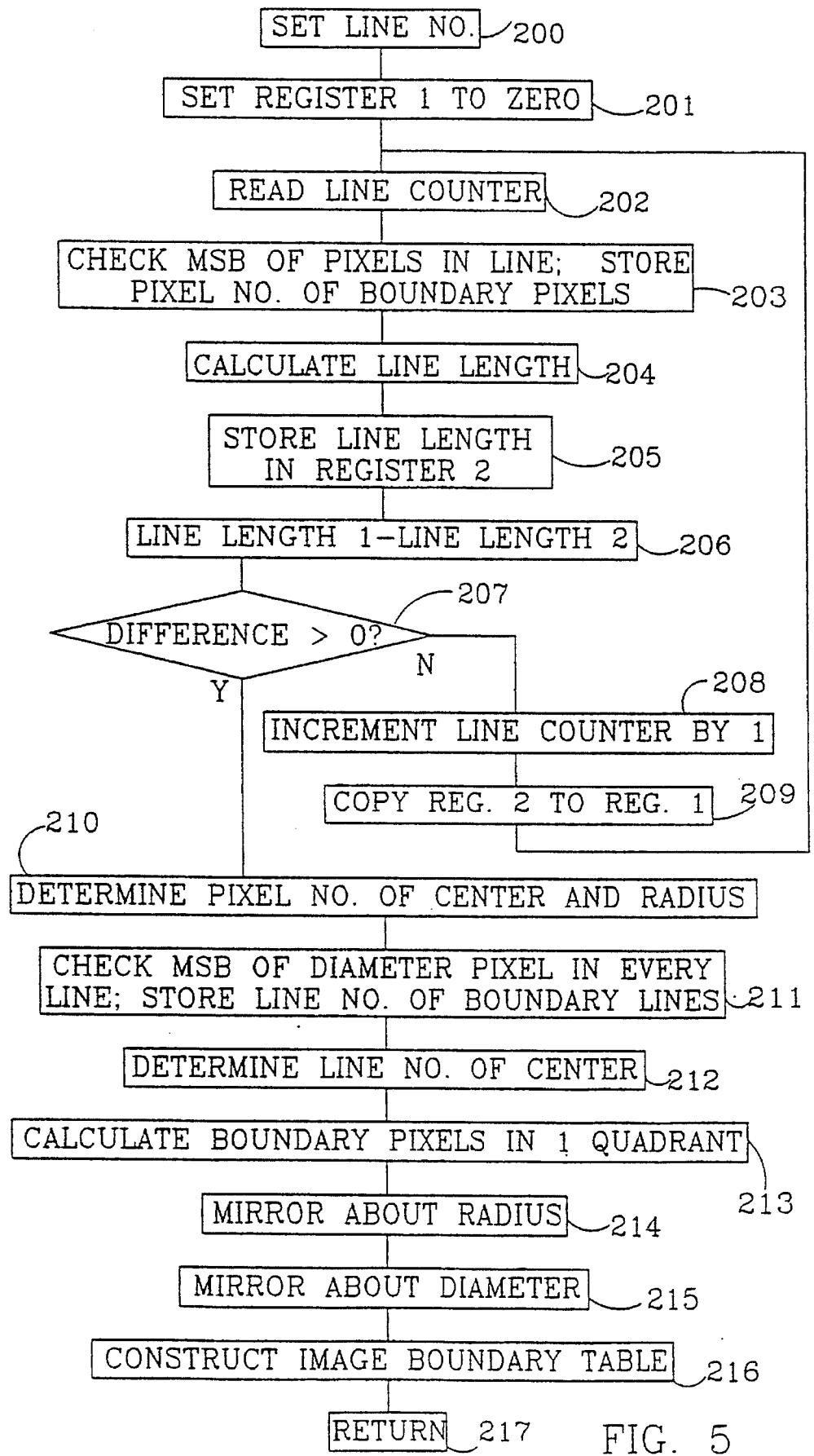
FIG. 5 shows a flow chart of the set-up routine in a video-based fibre-optic imaging system according to the invention.

The set-up routine shown in FIG. 5 assumes that a circular image is roughly centered on the CCD array. The routine could also be adapted to operate an image that has a known, but non-circular, shape. The routine first determines the radius of the image and the line number and pixel number corresponding to the center of the image. From this data, the routine generates values for an image boundary table by calculating the pixel numbers of the two boundary pixels on each line on which the image falls.

Figure 6A:
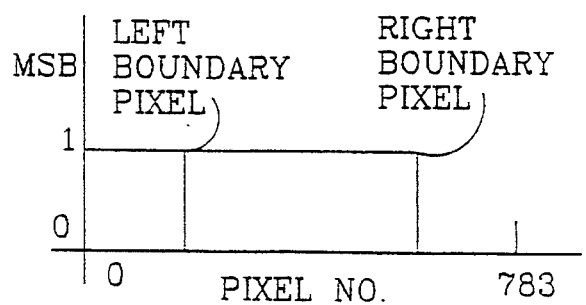
FIG. 6A is a graph showing the state of the most significant bit of the sample derived from each pixel along one line on which the image falls.

The state of the most significant bit (MSB) or some other high-order bit, of the samples corresponding to the pixels on each line on which the image falls has the form shown in FIG. 6A. The MSB changes state at the two points on the line corresponding to the boundary of the image falling on the line. The pixel number of the boundary pixel, at which the MSB changes state, changes from line-to-line.

In step 200, the DSP 153 sets the value stored in a line counter to a predetermined value corresponding to the line number of a line above the center of the CCD array. In step 201, the DSP sets the line length stored in a first register to zero. In step 202, the DSP reads the value stored in the line counter.

In step 203, the DSP 153 examines the state of the MSB of the sample for each pixel in the line having a line number defined by the line counter, and stores the pixel numbers of the two boundary pixels at which the MSB changes state in a second register.

At step 204, the DSP 153 calculates the difference between the two pixel numbers determined in step 203. This difference will be called the line length. The line length of a line indicates the number of pixels in the line on which the image falls. At step 205, the DSP stores the line length, also in the second register.

At step 206, the digital signal processor subtracts the line length stored in the second register from the line length stored in the first register. At step 207, the DSP tests whether the result of the subtraction is greater than or equal to zero. In this first iteration of the routine, the test result is NO, because of the initial value of zero stored in the first register. Accordingly, the routine proceeds to step 208, where the line counter is incremented by 1, and to step 209, where all the values in the second register are copied into the first register, after which execution returns to step 202.

In the second and subsequent iterations, at step 202, the DSP 153 reads the value in the line counter, and at step 203, the DSP examines the state of the MSB of the sample of each pixel in the "current" line which is the line having a line indicated by the value in the line counter. The current line is the line below the "previous" line, which is the line examined in the previous iteration. The DSP determines the pixel numbers of the two boundary in the current line at which the MSB changes state. At step 204, the digital signal processor calculates the line length of the current line by taking the difference between the two pixel numbers, and at step 205 stores the line length of the current line in the second register.

At step 206, the digital signal processor subtracts the line length stored in the second register (i.e., the line length of the current line) from the line length stored in the first register (i.e., the line length of the previous line). When, at step 207, the DSP tests whether the resulting difference is greater than or equal to zero, the result will be NO if the line length of the current line is greater than the line length of the previous line. This occurs when the previous line and the current line are both above the line corresponding to the diameter of the image. In this case, execution proceeds to steps 208 and 209, and then reverts to step 202.

If the subtraction at step 206 produces a positive or zero result, and the result of the test at step 207 is YES, this indicates that the line length of the current line is less than or equal to the line length of the previous line. This occurs when the current line and the previous line bridge the diameter of the image (zero result) or when the current line is one line below the diameter, and the previous line is the diameter. In this case, execution passes to step 210, where one is subtracted from the value of the line counter, and the result is stored as the line number of the center of the image. The pixel number of the center of the image is determined by subtracting the left boundary pixel number stored in the first register from the right boundary pixel number stored in the first register, i.e., the boundary pixel numbers of the previous line. The difference is divided by two to provide the radius of the image. The radius is then added to the left boundary pixel number to determine the pixel number of the center of the image.

The part of the algorithm just described accurately determines the radius of the image, and the pixel number of the center of the image, but, because the line length changes relatively slowly in the vicinity of the diameter, the line number of the center of the image is less accurately determined. The next part of the algorithm accurately determines the line number of the center of the image.

Figure 6B:
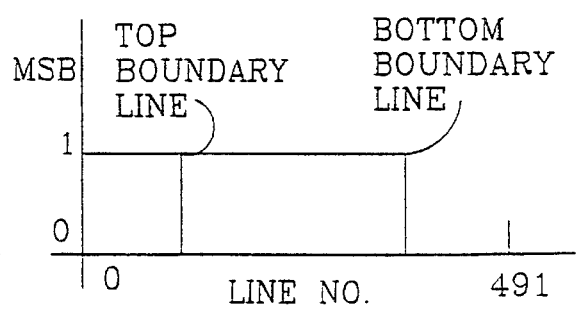
FIG. 6B is a graph showing the state of the most significant bit of the sample derived from the pixel having a pixel number equal to the pixel number of the center of the image on each line of the frame.

In step 211, the DSP 153 examines the state of the MSB of the sample in each line corresponding to the pixel having the same pixel number as that the center of the image determined in step 210. The state of the MSB of the pixels having the same pixel number in each line has the form shown in FIG. 6B. The DSP stores the line numbers of the top and bottom boundary lines, at which the MSB changes state.

At step 212, the DSP 153 determines the line number of the center of the image by subtracting the top line number from the bottom line number, dividing the resulting difference by two, and adding the resulting quotient to the top line number. This step may also provides the radius of the image, and may compare this radius with the radius calculated in step 210. If the two results do not agree, steps 202 through 210 can be repeated. Alternatively, the accuracy of the image boundary calculation performed in the following steps can be increased by regarding the image as an ellipse, and using the radii calculated in steps 210 and 212 as the axes of the ellipse.

In step 213, the pixel number of one boundary pixel, e.g., the left boundary pixel, on each line corresponding to a quadrant of a circle or ellipse are calculated for each line from the center and radius calculated in steps 210 and 212.

In step 214, the pixel number of the other boundary pixel, e.g., the right boundary pixel, in each line for one half of the image is calculated by mirroring the pixel numbers calculated in step 213 about the radius of the image. Finally, in step 2 15, the pixel numbers of both boundary pixels in each line in the rest of the image are calculated by mirroring the pixel numbers calculated in steps 213 and 214 about the diameter of the image.

As an alternative to the line-by-line and pixel-by-pixel approach just described, a routine similar to that just described could be used to find the pixel numbers of the boundary pixels on several lines in the image sensor. Then, a curve fitting routine could be used to determine the pixel numbers of the boundary pixels on all lines in the image, and the line number and pixel number of the pixel corresponding to the center of the image.

The results of the above calculations are placed in the image boundary table stored in the RAM 157. As described above, the image boundary table preferably consists of a number pair for each boundary line, plus an additional number pair. The additional number pair consists of the line numbers of the top and bottom boundary lines. These line numbers are determined in step 212. The rest of the number pairs consist of a number pair for each boundary line between the top boundary line and the bottom boundary line, inclusive. Each number pair consists of the pixel numbers of the left and right boundary pixels of the line. Alternatively, a number pair can be stored for each line, irrespective of whether the line is a boundary line. The number pair for each line which is not a boundary line would include a number outside the range of pixel numbers, e.g., greater than 784, to indicate that the line is not a boundary line.

Once the set-up routine has been completed, the digital signal processor returns to its main routine.

2. Basic Image/External Area Processing Routine

In this process, the digital signal processor (DSP) 153 performs the processing which stores the sample values of only those pixels on which the image falls in the corresponding memory locations in the frame store 155. For the pixels in the external area of the frame, surrounding the image, the DSP stores a predetermined value in the corresponding memory locations in the frame store 155. The predetermined value could be a value corresponding to black level, a level corresponding to a predetermined luminance and/or hue, and may vary according to the position of the pixel in the external area.

Figure 7A:
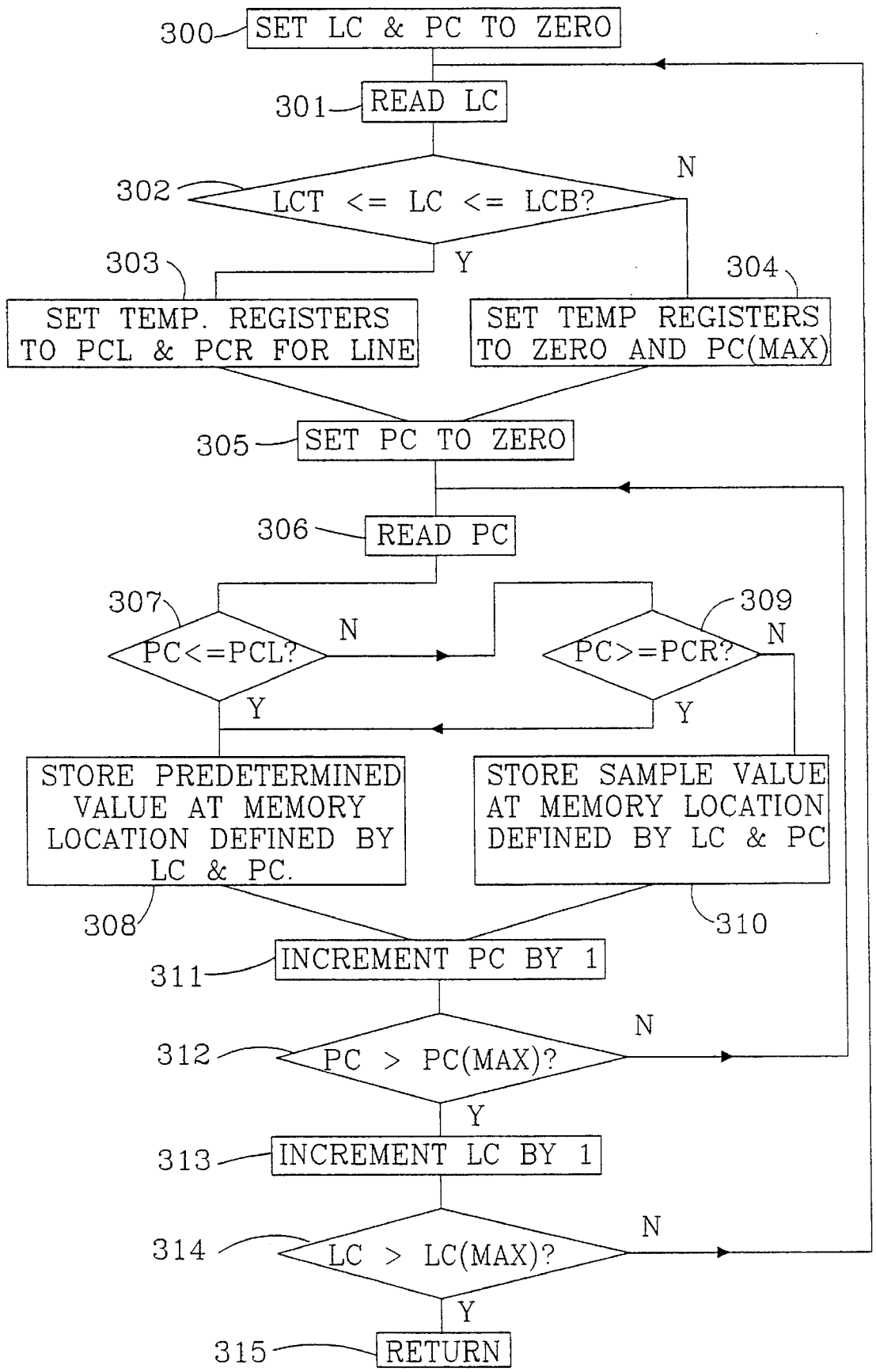
FIG. 7A is a flow chart showing the main routine by which samples from the external area are processed differently from samples from the image in a video-based fibre-optic imaging system according to the invention.

To apply different processing to the image and the external area, the DSP 153 processes each frame of the digital video signal received from the analog-to-digital converter 183 using the routine shown in FIG. 7A. In step 300, the digital signal processor initializes a line counter LC and a pixel counter PC to zero. The line counter and the pixel counter can be registers in the DSP, or can be memory locations in the RAM 157. Also in this step, the DSP resets the image sensor array 151 (FIG. 3A).

In step 301, the DSP 153 reads the line number from the line counter, and in step 302, the DSP determines whether the line is a boundary line. In the preferred embodiment, the DSP makes this determination by using steps similar to steps 307 and 309, to be described below, to test whether the line number lies between the line numbers of the top boundary line and the bottom boundary line. These values are found in the additional number pair in the image boundary table stored in the RAM 157.

If the line is a boundary line, at step 303, the DSP copies the first of the number pair for the line (the pixel number PCL of the left boundary pixel) from the image boundary table to a first register, and the second of the number pair for the line (the pixel number PCR of the right boundary pixel) from the image boundary table to a second register.

If the line is not a boundary line, execution passes to step 304, where the DSP 153 sets value in the first register to zero, and the value in the second register to a number equal to the maximum number of pixels PC(MAX) in a line, e.g., to 783 (the first pixel is pixel 0).

At step 305, the DSP 153 sets a pixel counter PC to zero. At step 306, the DSP reads the pixel number from the pixel counter. At step 307, the DSP tests whether the value in the pixel counter is less than or equal to the value in the first register. If the result is YES, indicating that the pixel is in the external area, execution passes to step 308, where the DSP ignores the sample value for the pixel received from the analog-to-digital converter 183, and instead stores a predetermined value in the frame store 155 at the memory location defined by the current values of the line counter and the pixel counter. The predetermined value, which, for example, is a value corresponding to black level, will be described in detail below. Execution then passes to step 311.

If the result at step 307 is NO, execution passes to step 309, where the DSP 153 tests whether the value in the pixel counter is greater than or equal to the value in the second register. If the result is YES, this indicates that the pixel is in the external area, and execution passes to step 308, where the DSP ignores the sample value for the pixel received from the analog-to-digital converter 183, and instead stores a predetermined value in the frame store 155 at the memory location indicated by the current values of the line counter and the pixel counter, as described above.

If the result in step 309 is NO, the pixel number is greater than the pixel number of the left pixel number and less than the pixel number of the right pixel number, which indicates that the pixel is a pixel on which the image falls. Accordingly, execution passes to step 310, where the DSP 153 stores the sample value for the pixel received from the analog-to-digital converter 183 (FIG. 3A) at the memory location in the frame store 155 indicated by the current values of the line counter and the pixel counter.

At step 311, the DSP increments the value of the pixel counter by 1, and at step 312, tests whether value in the pixel counter is greater than the maximum pixel number PC(MAX), e.g., >783. If the result is NO, indicating that the new pixel number corresponds to a pixel on the line, execution returns to step 306, where the next pixel is processed. Otherwise, and the result is YES, execution advances to step 313, at which the DSP increments the value in the line counter by 1, and tests, at step 314, whether the value in the line counter is greater than the maximum line number LC(MAX), e.g., >491. If the result is NO, execution returns to step 301 to process the next line. Otherwise, and the result is YES, indicating that all the lines in the frame have been processed, execution advances to step 315, which returns execution to the main routine.

A result similar to that achieved by the processing just described may be provided by feeding all the samples in one frame of the digital video signal from the analog-to-digital converter 183 into the frame store 155 without processing them, and then applying processing similar to that just described when the DSP 153 reads the stored samples out of the frame store. In this case, the DSP generates the digital video output signal directly from the sample value in the frame store for each pixel on which the image falls. For each pixel in the external area, the DSP ignores the stored sample value for the pixel, and instead generates the appropriate predetermined value, and from it, the digital video output signal.

3. Position-Dependent Image Gain Correction

In some endoscope designs, the intensity of the image formed on the image sensor in the remote camera head may fall off towards the boundary of the image. The video-based fibre-optic imaging system according to the invention can apply a preset radial gain correction algorithm, a radial gain correction determined from the image, or a radial gain correction set by the user, to create a more uniform image intensity. Instead of a simple radial variation, the video-based fibre-optic imaging system according to the invention may alternatively apply a more general position-dependent gain correction algorithm to the image area. The techniques to be described next can also be used to provide a non-uniform radial intensity pattern, should this be desired. Radial or position-dependent gain compensation can easily be applied in an imaging system according to the invention since the boundary and the center of the image on the sensor is known.

Figure 7B:
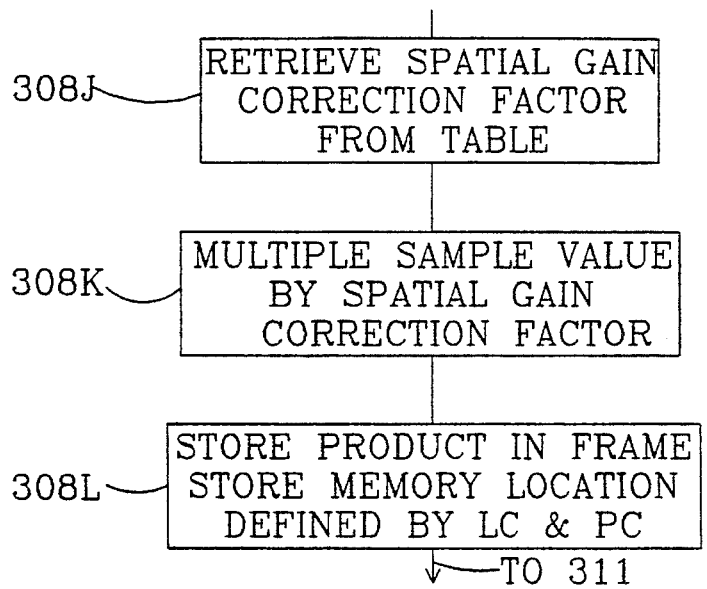
FIG. 7B is a flow chart showing how step 310 of the routine shown in FIG. 7A is modified to apply a radial gain correction.

A technique for applying radial gain correction will be described as an example of applying a more general position-dependent gain correction to the image. The video-based fibre-optic imaging system according to the invention can apply position-dependent gain correction by modifying step 310 of the routine shown in FIG. 7A. Alternatively, the correction can be applied when the sample data is read out of the frame store 155. In the modified step 310, shown in FIG. 7B, at step 310J, the DSP 153 retrieves the radial gain correction factor for the pixel from the address corresponding to the pixel in a radial gain correction factor table stored in the RAM 157. Then, at step 310K, the DSP multiplies the sample value for the pixel defined by the line number and the pixel number by a radial gain correction factor. Finally, at step 310L, the DSP stores the resulting product in the frame store 155 at the memory location defined by the line number and pixel number of the pixel.

A radial gain correction factor is determined for each pixel in the image during the set up procedure described above, and is stored in a radial gain correction factor array in the RAM 157 for use in the modified step 310. To determine the radial gain correction factor for each pixel, the DSP 153 may, for example, download from the memory in the fibre-optic assembly the entire radial gain correction factor array, or may download an algorithm or look-up table defining the radial variation of sensitivity from a memory in the fibre-optic assembly. Alternatively, the DSP may look up the entire radial gain correction array, or an algorithm or look-up table defining a radial variation of sensitivity in response to information defining the type of endoscope retrieved by the fibre-optic data unit 185. Retrieving information or identification information from the fibre-optic assembly is discussed in Section 1(a) above.

If information defining the radial variation of sensitivity is used, the DSP 153 would first normalize this information to the radius of the image determined during the set up procedure. Then, for each line in the image, the DSP would calculate the distance of each pixel on the line from the center of the image. This is done by subtracting the line number of the center of the image from the line number of the line, subtracting the pixel number of the center from the pixel number of the pixel, squaring the resulting differences, and adding them. Then, using this distance, the DSP would calculate using the normalized algorithm, or look up in the normalized look-up table, the radial gain correction factor for the pixel. The DSP would store the calculated radial gain correction factor in the radial gain correction factor array at the address defined by the line number and pixel number of the pixel.

As an alternative to the information defining the radial variation of sensitivity being derived from an algorithm or a look-up table, the user could enter a radial variation of sensitivity using the control panel 187. The user could point to a point on the image displayed on the monitor using a suitable pointing device, such as a mouse, or a touch screen, and could then enter a gain change, or increment or decrement gain using arrow keys, to set the desired radial variation of sensitivity. The DSP would then interpolate between the points set by the user to derive a table of gains to use in calculating the radial gain correction factor for each pixel.

As an alternative example, during the set-up procedure described above, the distal tip of the fibre-optic assembly would be directed at a uniformly-illuminated target, and the DSP 153 would execute a radial gain normalization routine. In the gain normalization routine, the DSP would derive a radial gain correction factor for each pixel in the image. The DSP would determine the radial gain correction factor by measuring the factor by which the sample value generated by the pixel in response to the uniformly-illuminated target is multiplied to reach a predetermined level. The predetermined level is determined by taking the average of a block of sample values generated in response to the uniformly-illuminated target in the center of the image.

The DSP would first examine the contents of a block of, for example, 16×16 memory locations symmetrically disposed about the center of the image. The DSP would generate a predetermined value representing the average illumination level in this central block by adding the values stored in these memory locations together, and dividing the result by 256. Then, for each line in the image and for each pixel in the image in the line, the DSP would divide the value representing the average illumination level by the value stored in the frame store 155 at the memory location corresponding to that pixel. The DSP would store the resulting quotient as the radial gain correction factor for the pixel in the radial gain correction factor array in the RAM 157 at the address defined by the line number and the pixel number of the pixel.

4. Luminance Control

In this aspect of the invention, the image processing electronics 101 of the video-based fibre-optic imaging system according to the invention generate a control video signal or a servo control signal in response to the image. The control video signal or the servo control signal then can be used to control an existing automatic luminance control system in response to the luminance level of the image. The automatic luminance control system may be the automatic electronic shutter in the camera. However, with small-diameter endoscopes, especially when operating at hyperextended working distances, it is preferred that the control video signal or the servo control signal be fed into the control system of a video signal-controlled variable-intensity light source.

Controlling the intensity of the light source is preferred since it allows a greater maximum light intensity to be used. This, in turn, provides a greater signal-to-noise ratio in images of distant objects. The precision of light intensity control afforded by the control video signal and servo control signal allows a greater maximum light intensity to be used without the risk of overheating the optical fibres of the fibre-optic assembly when the distal end of the fibre optical assembly contacts an object or tissue. The control video signal or the servo control signal automatically reduces the intensity of the light as the distal end of the fibre-optic system approaches an object or tissue. By the time that the distal end of the fibre-optic system is close enough to contact the object or tissue, the intensity of the light has been reduced to a level well below that which can cause the distal end of the fibre-optic system to overheat if contact occurs.

(a) Control Video Signal Generation

In this aspect of the invention, the image processing electronics 101 generate, in response to the image, a control video signal that can be fed into an automatic luminance control system, such as the automatic shutter in the camera. However, it is preferred that the automatic shutter system in the camera be set to a fixed shutter speed, and that the control video signal be fed into the control system of a known video signal-controlled variable-intensity light source.

As discussed above, the intensity control systems in such known light sources respond to the luminance level of the whole video frame, and thus operate incorrectly in response to a frame consisting of an image surrounded by a blank external area. In response to the luminance of the image only, the video-based fibre-optic imaging system according to the invention synthesizes a control video signal that emulates filling the whole frame with a video signal similar to the video signal in the image. Known variable-intensity control systems then respond to the synthesized video signal as they would to a video signal produced by an image filling the whole frame.

Figure 8:
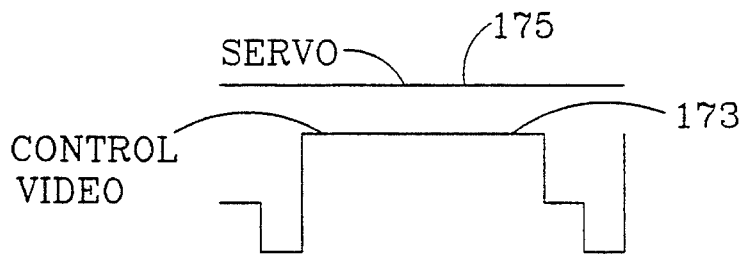
FIG. 8 shows one line of the control video signal and the corresponding servo signal generated in response to the video signal shown in FIG. 1C in a video-based fibre-optic imaging system according to the invention.

The DSP 153 generates the digital control video signal 161 in response to sample values of the image portion of the frame stored in the frame store 155. The digital control video signal 161 is also converted to an analog control video signal 173 by the digital to analog converter 167, to produce the analog control video signal. The appropriate one of the digital control video signal and the analog control video signal is fed into the variable-intensity light source 103. FIG. 8 shows one line of a typical control video signal generated in response to the typical line shown in FIG. 1C.

Since known variable intensity control systems respond to the average intensity in the whole frame, and are insensitive to the distribution of intensity in the frame, a first embodiment of the control video signal generator synthesizes a control video signal in which each frame is filled repetitions of the image. The resulting control video signal is scrambled, but this does not matter to the intensity control circuit in the variable-intensity light source.

In the first embodiment, the DSP 153 sequentially reads the sample values of the image stored in the frame store 155 and inserts them sequentially into the frame of the digital control video signal. Part-way through generating the frame of the digital control video signal, the DSP comes to the end of all the samples in the image. When this occurs, the DSP returns to the first sample in the image, reads out the sample values of the image once more, and inserts them into the frame of the digital control video signal, starting from where the samples from the first reading of the image ran out. The DSP reads the samples in the image as many times as is required to generate a full frame of the digital control video signal. The DSP then repeats the process just described to generate the next frame of the digital video control signal.

Figure 9:
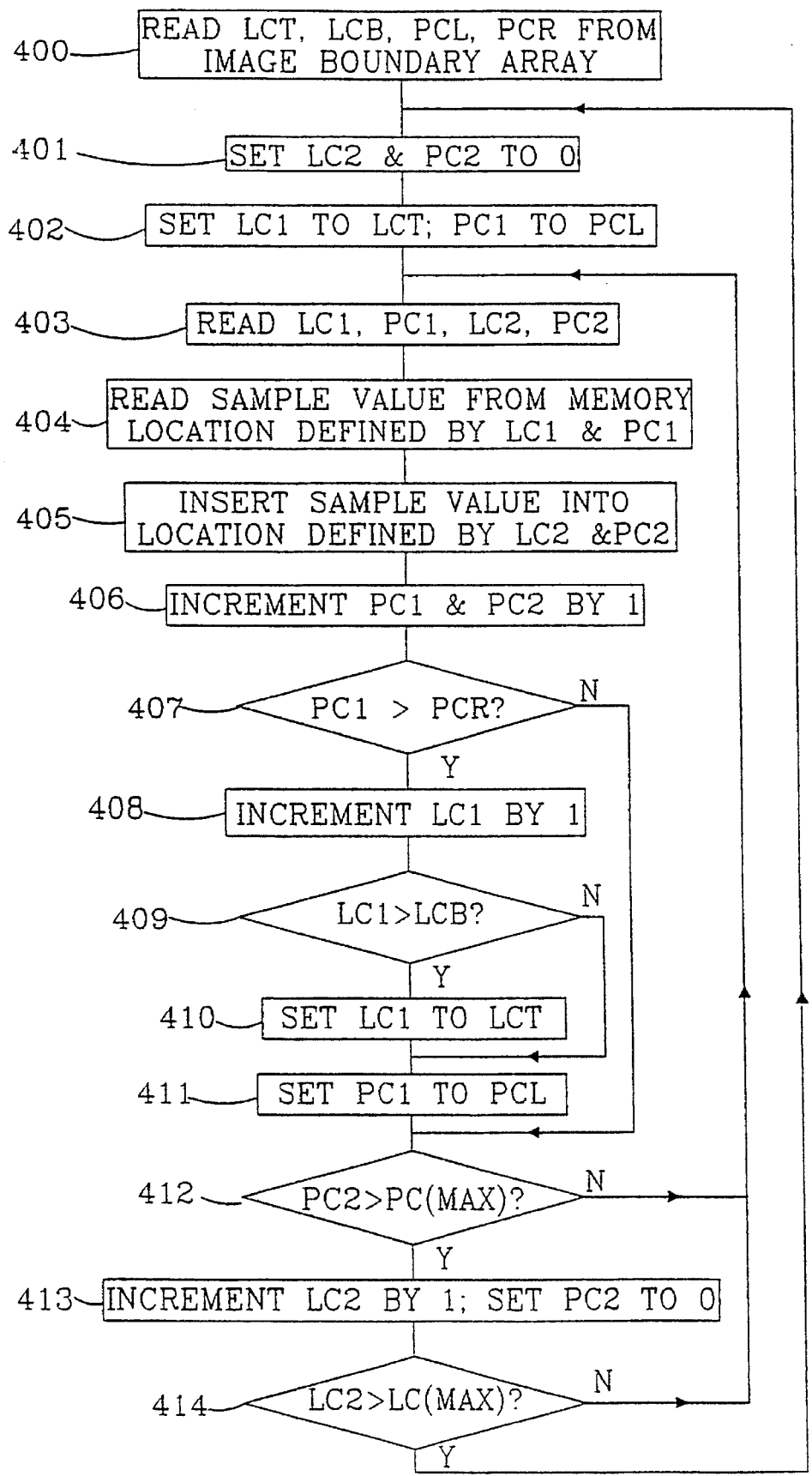
FIG. 9 is a flow chart showing the routine by which the digital signal processor generates a first type of control video signal in a video-based fibre-optic imaging system according to the invention with a variable intensity lamp-based automatic luminance control system.

The routine by which the DSP 153 generates a first type of digital control video signal is shown in FIG. 9. In step 400, the DSP reads from the image boundary array generated during the set-up procedure the line numbers, LCT and LCB, of the top and bottom lines, respectively, of the image, and the pixel numbers, PCL and PCR, of the left and right boundary pixels, respectively, of the top line of the image. In step 401, the DSP sets an output line counter LC2 and an output pixel counter PC2 to zero. In step 402, the DSP inserts the line number LCT of the top line and the pixel number PCL of the left boundary pixel into an input line counter LC1 and an input pixel counter PC1, respectively. The input and output line counters and pixel counters can be registers in the DSP, locations in the RAM 157, or other suitable memories.

In step 403, the DSP 153 reads the values in the input line counter and pixel counter and in the output line counter and pixel counter. At step 404, the DSP reads the sample value from the memory location defined by the values in the input line counter and the input pixel counter. At step 405, the DSP inserts this sample value into the frame of the digital control video signal at a location defined by the values in the output line counter and the output pixel counter.

At step 406, the DSP 153 increments both pixel counters by 1. At step 407, the DSP tests whether the next pixel is in the image by testing whether the value in the input pixel counter is greater than the pixel number of the right boundary pixel for the line indicated by the line number in the input line counter. If the result is NO, execution passes to steps 412 through 414, where the value in the output pixel counter is tested. Otherwise, and the result is YES, execution passes to step 408, where the DSP increments the input line counter by 1.

At step 409, the DSP 153 tests whether the new line is in the image by determining whether the value in the input line counter is greater than the line number of the bottom line of the image. If the result is NO, execution passes to step 411, which will be described below. Otherwise, and the result is YES, execution passes to step 410, where the DSP copies into the input line counter the line number of the top line of the image. Execution then proceeds to step 411.

At step 411 the DSP 153 copies into the input pixel counter the pixel number of the left boundary pixel of the line indicated by the value of the input line counter.

The YES result at step 407 indicates that all the sample values in the current line of the image have been copied to the digital control video signal. Steps 408, 410, and 411 together cause the routine to start coping sample values from the left boundary of the image in the next line to the digital video control signal.

The YES result at step 409 indicates that all the sample values in the current frame of the image have been copied into the digital control video signal. Steps 410 and 411 together cause the routine to start once more to copy sample values from the top of the image to the digital video control signal.

At step 412, the DSP 153 tests whether the value in the output pixel counter PC2 is greater than the number of pixels PC(MAX) in the line of the digital control video signal, e.g., >784. If the result is NO, execution returns to step 403. Otherwise, and the result is YES, execution passes to step 413, where the DSP increments the output line counter by 1 and sets the output pixel counter to zero. At step 414, the DSP tests whether the value in the output line counter LC2 is greater than the number of lines LC(MAX) in the digital control video signal frame, e.g., >492. If the result is NO, execution passes to step 403, where construction of the current frame of the digital video control signal continues. Otherwise, and the result is YES, execution returns to step 401, where the routine starts to generate the next frame of the digital control video signal.

The YES result at step 412 indicates that the current line of the digital video control signal has been filled with sample values. Step 413 causes the routine to start to copy sample values to the beginning of the next line of the digital video control signal.

The YES result at step 414 indicates that the frame of the digital video control signal has been filled with sample values. Consequently, execution returns to step 401 to allow the routine to start generating the next frame of the digital video control signal.

Each frame of the resulting digital control video signal, after it has been converted to an analog signal by the digital to analog converter 167, has an average luminance level equal to the average luminance level in the image. The video control signal thus emulates a control video signal resulting from a fully-illuminated frame having an average luminance level equal to the average luminance level of the image.

Processing can be simplified by reducing the number of pixels in each line of the control video signal, since the resolution of this signal is unimportant.

In a second embodiment of generating the control video signal, the DSP 153 can use known digital signal averaging techniques to derive, for each frame, an average sample value for the image. The DSP can then generate the digital video control signal in which every sample value in the frame is equal to the average sample value. Each frame of the resulting digital control video signal, after it has been converted to an analog signal by the digital to analog converter 167, has a uniform luminance level equal to the average luminance level of the corresponding frame of the image.

In a third embodiment, the DSP 153 can, preferably during the set-up routine described above, calculate a ratio between the number of pixels in the frame of the digital video control signal, and the number of pixels in the image. This ratio could be stored for use in the following and other image processing functions. The DSP can then generate the digital control video signal by multiplying each sample value in the image by the ratio, and setting each pixel outside the image to a value corresponding to black level. This method may be less preferred than the methods just described because of the possibility of the increased amplitude of the digital control video signal saturating the digital-to-analog converter 167, and the following analog circuitry.

(b) Servo Signal Generation

In this aspect of the invention, the image processing electronics 101 generate, in response to the image, a servo signal that can be fed into an automatic luminance control system, such as the automatic shutter in the camera. However, it is preferred that the automatic shutter system in the camera be set to a fixed shutter speed, and that the servo signal be fed into the control system of a known video signal-controlled variable-intensity light source.

To generate the digital servo signal 163, the average sample value for each frame, derived as described above, is further processed by the DSP 153. The digital servo signal 163 is fed to the digital-to-analog converter 169, which converts it to the analog servo signal 175. The appropriate one of the digital servo signal 163 and the analog servo signal 175 is fed into the variable-intensity light source 103, where it directly controls the intensity of the variable-intensity light source. This allows the video signal-responsive servo circuit in the variable-intensity light source to be bypassed. The additional processing by the DSP would compare the average sample value with a reference level generated by the DSP in response to an intensity level set by user using the control panel 187, and would provide the resulting signal with dynamic (attack and decay) characteristics suitable for controlling the automatic luminance control system. The DSP would provide the resulting error signal as the digital servo signal 163.

(c) Reflective Object Rejection

As mentioned above, light reflected from highly-reflective objects cause known camera-based or light source-based average luminance level control systems to reduce significantly the luminance level of the whole of the frame. This can cause the part of the frame being observed by the surgeon to disappear into black level. Time must then be wasted repositioning the reflective object and/or the endoscope, or adjusting the video system, to remove the reflective object from the field of view.

The video-based fibre-optic imaging system according to the invention may be modified to reduce the responsiveness of the luminance control system to light reflected from localized, highly reflective objects, while retaining the responsiveness of the control systems to the overall luminance level of the image. Retaining responsiveness the overall luminance level of the image is essential to enable the safe use of a maximum light intensity capable of overheating the fibre-optic assembly.

The inventor has discovered that luminance level changes that result from the tip of the fibre-optic assembly approaching an object or tissue take place more or less uniformly over the extent of the image, whereas luminance level changes due to a highly-reflective object are localized in a portion of the image. Using the method described above for controlling the luminance level in response to the luminance level in a central portion of the image sensor does not reliably provide a satisfactory degree of discrimination: image black out will occur if the highly reflective object is located in the center of the sensor.

The video-based fibre-optic imaging system with reflective object rejection according to the invention divides the image into plural sectors, determines the average luminance level in each sector, determines relationships between the average luminance levels in each sector, and generates a control video signal and/or a servo signal for controlling the luminance control system in response to the determined relationships.

Figures 10A, 10B:
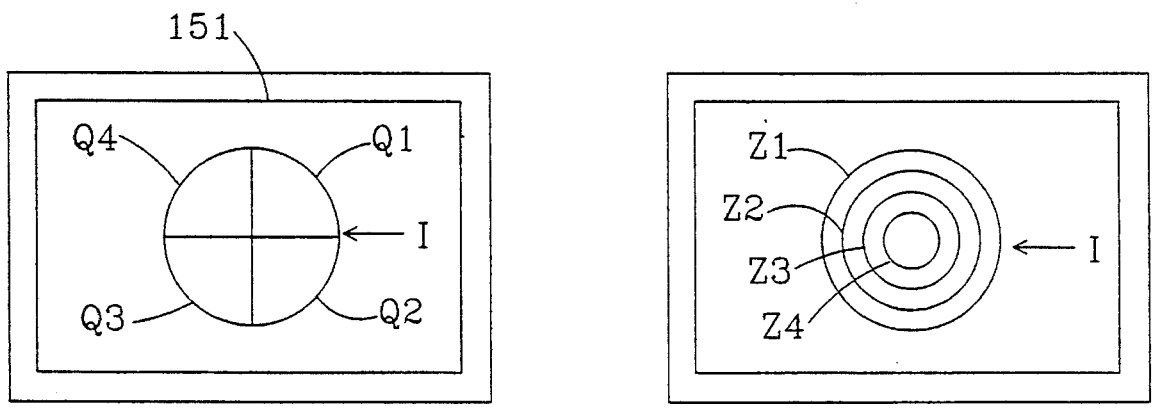
FIG. 10A shows how the image is divided into quadrants in a video-based fibre-optic imaging system according to the invention with an automatic luminance system with reflective object rejection.
FIG. 10B shows how the image is divided into radial zones in a video-based fibre-optic imaging system according to the invention with an automatic luminance system with reflective object rejection.

An embodiment of the reflective object rejecting automatic luminance control system according to the invention divides the image I into four quadrants $Q_1$ through $Q_4$, as shown in FIG. 10A. Greater discrimination can be obtained at the expense of greater processing complexity by dividing the image into a greater number of sectors. With the simple arrangement of quadrants shown in FIG. 10A, the interquadrant boundaries are defined by the line number and the pixel number of the center of the image determined during the set-up procedure described above.

Using a known averaging algorithm, the DSP 153 calculates an average luminance for each quadrant. The DSP then examines the average luminance of the quadrants, and generates the control video signal or the servo signal in response. This can be done in different ways. For example, the DSP can generate an average of the four averages. Then, the DSP can determine a localization index for each quadrant by, for example, determining the ratio of the difference between the average luminance of the quadrant and the average of the averages and the sum of the average luminance of the quadrant and the average of the averages. The DSP can then weight the average luminance of each quadrant inversely to the localization index for the quadrant, and derive an average of the weighted averages as the average sample value. The DSP would then derive the control video signal and/or the servo signal from the average sample value, as described above.

Alternatively, the DSP 153 could calculate the average sample value by taking an average of the averages of only those quadrants whose localization indices remain below a threshold level.

The DSP 153 could alternatively derive the localization index for each quadrant by determining the ratio of the difference between the average luminance of the quadrant and the average luminance of the adjacent quadrant, and the sum of the average luminance of the quadrant and the average luminance of the adjacent quadrant.

The DSP 153 could also apply fuzzy logic to derive the localization index and to deriving the control signal and/or the servo signal from the average luminance levels of the quadrants.

The DSP 153 could alternatively derive the average sample value, and hence the control video signal and/or the servo signal, from the average luminance levels of the quadrants by comparing the localization index determined as described above, or otherwise, with a threshold, and deriving the average sample value by multiplying the average of the averages by a factor that depends on the number of the four localization indices that exceeds the threshold. When, for example, only one of the localization indices exceeds the threshold, the factor is such that the change in the light intensity resulting from a given change in the average luminance is considerably less than when all the localization indices exceed the threshold. This makes the light intensity less responsive to high levels in only one quadrant.

Finally, the DSP could apply windowing and thresholding to the average illumination levels when combining them. For example, the DSP would only change the combined average illumination level if the average illumination levels of sectors representing more than a predetermined fraction (e.g., 25%) of the image changed relative to the present value of the combined average illumination level.

The techniques described above could alternatively or additionally be applied to the arrangement shown in FIG. 10B, in which the image I is divided into radial zones, such as the radial zones Z1 through Z4.

Finally, the DSP 153 could apply histogram averaging to the whole image, or to quadrants or radial zones of the image. To apply histogram averaging the DSP first calculates the distribution of luminances, i.e., determines the number of pixels having a luminance in a given range. From this, the DSP can determine a predominant luminance range, and can then determine a function by which to modify luminance levels in luminance ranges remote from the predominant luminance range so that they lie within a predetermined range of the predominance luminance range.

The techniques described above generate the control video signal and/or servo signal in response to the luminance of the image, but with a reduced sensitivity to parts of the image having a luminance that differing by greater than a threshold amount from that of the rest of the image. With such techniques, light reflected from a high-reflectivity object reduces the luminance of the image to a lesser extent, so that the part of the image being observed by the surgeon remains visible.

6. Noise Reduction

Even with the improved illumination levels offered by the video-based fibre-optic imaging system according to the invention, at extended working distances, noise can be noticeable in low-level parts of the image. By using additional pages in the frame store 155 (FIG. 3A), the DSP 153 can apply video averaging to improve the signal-to-noise ratio of the picture. Adding together the sample values for the same pixel in consecutive frames of the video signal provides a 3 dB improvement in signal-to-noise ratio. Adding a the sample values for the next two consecutive frames improves the signal-to-noise ratio by a further 3 dB.

If the object were completely static, the sample values from additional frames could be added to achieve yet further improvements in signal-to-noise ratio. In practice, however, the object is not static, and the number of sample values that can be added to achieve an improvement in signal-to-noise ratio is limited by smearing resulting from the sample values changing as a result of motion in the object.

The video-based fibre-optic imaging system according to the invention reduces noise by summing the sample values for the same pixel in consecutive flames over a number of flames. The number of flames over which averaging takes place may be fixed, or may be dynamically determined according to the dynamics of the object. The dynamic determination may be made for the whole image, or for individual pixels or groups of pixels within the image.

Figure 3B:
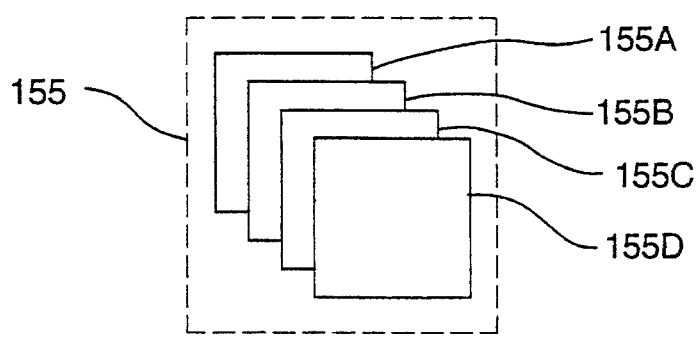
FIG. 3B shows a modification to the frame store in the image processing electronics shown in FIG. 3A. The modification provides video noise reduction in a video-based fibre-optic imaging system according to the invention.

The video-based fibre-optic imaging system with noise reduction according to the invention can be realized using the arrangement shown in FIG. 3A, except that the frame store has multiple pages 155A through 155D, as shown in FIG. 3B. In this example, averaging is applied over a maximum of four flames. The number of pages can be increased to increase the number of flames over which averaging takes place, if desired. The noise reduction techniques to be described below can also be applied to images occupying the full area of the image sensor 151 in the camera, if desired. If noise reduction is to be applied only to images produced by small-diameter endoscopes, i.e., by images occupying less than the full area of the sensor 151, the cost of the frame store may be reduced by reducing the number of memory locations in each page to that corresponding to the number of pixels in the largest image formed on the sensor.

The DSP 153 feeds the samples generated by the analog-to-digital converter 183 in consecutive flames of the output of the image sensor 151 into the consecutive pages 155A through 155D of the frame store 155. When the DSP has filled the fourth page 155D with samples, the DSP overwrites the first page 155A with the samples of the fifth frame, and so on. The DSP can process the samples generated by the analog-to-digital converter using one or more of the techniques described above before storing the processed samples in the frame store.

In a first embodiment, the DSP 153 generates each pixel value in each frame of the output signal by reading the sample value for the pixel having the same line number and pixel number in each page of the frame store 155, summing the four sample values for the pixel, dividing the result by four by using, for example, two right shifts, and using the result as the sample value for the pixel. The DSP repeats this process for all the other pixels in the image. The DSP combines the sample values for the pixels in the image with the fixed values for the external area and generates one frame of the digital video output signal 171 from the result.

After filling all the flames in the frame store with sample values, in the next frame period, the DSP stores the next frame of sample values from the analog-to-digital converter in the first page of the frame store 155, overwriting the sample values written four frame periods ago, and generates the next frame of the digital video output signal 171 by averaging, for each image pixel, the four flames of sample values currently stored in the frame store.

This embodiment improves the signal-to-noise ratio of the picture by about 6 dB, but motion in the object causes smearing of edges in the picture. Also, each output frame is delayed by 4 frame periods relative to the "oldest" samples it contains.

In the second embodiment, pixel averaging is applied dynamically to prevent smearing when the object moves. In this embodiment, pixel averaging is applied over four frames only when the object is static. When movement in the object is detected, the number of frames over which averaging is applied is reduced, or averaging is suspended altogether. This increases the signal-to-noise ratio of the picture, but the motion in the object makes the increased signal-to-noise ratio less noticeable than the same signal-to-noise ratio in a static picture.

The DSP 153 stores sample values from the analog-to-digital converter 183 into consecutive pages of the frame store 155, as described above. The DSP then checks the stored sample values for motion. This can be done in a number of ways. For example, the DSP can check whether, for a number of test pixels located at various points throughout the frame, the four stored sample values lie within an allowable range. To avoid the averaging decision being confused by noise in the low-level parts of the image, test pixels having a sample value less than a predetermined threshold are ignored. If the four pixel values lie within the allowed range, the DSP averages all the pixels in the image over four flames, as described above. Otherwise, the DSP checks whether the three most recent sample values lie within the allowable range. If they do, the DSP averages all the pixels in the image over the three most recent flames. Otherwise, the DSP checks whether the two most recent sample values lie within the allowable range. If they do, the DSP averages all the pixels in the image over the two most recent flames. Otherwise, no averaging is applied, and the DSP simply reads out the most recently-stored frame.

The processing just described can be simplified by storing prior history information for each of the sample locations. Then, for example, if, in the previous frame, the DSP read out only the most recent frame (no averaging), there would be no point in checking samples other than those for the two most recent frames in the current frame. Alternatively, the DSP can average all the pixels in the image for those flames whose test pixels lie within an allowable range.

A third embodiment operates similarly to the second embodiment, except that the averaging decision is made individually for each pixel in the image. This localizes the areas in which no noise reduction is applied to parts of the image in which there is actual motion, which increases the ability of the motion to mask the noise. To avoid the averaging decision being confused by noise in the low-level parts of the image, the averaging decision may be made individually for each pixel in the image having a sample value greater than a threshold value. An averaging decision for pixels in the lower-level parts of the image can then be derived from the averaging decisions made for the pixels in the higher-level parts of the image.

The number of frames over which averaging is applied can also be manually selected by the operator, if desired.

Alternatively, a single additional page can be used in the frame store 155 to store an accumulation of the sample values in past frames for each pixel. With this arrangement, the DSP 153 multiplies the accumulated sample value stored in each memory location in the single additional page by a degeneration factor of less than unity and adds the multiplied accumulated sample value to the sample value for the corresponding pixel in the current frame. This sum is then divided by one plus the degeneration factor to normalize its amplitude, and the resulting quotient is used as the sample value for the pixel in the current frame. The resulting quotient is also stored in the additional page of the frame store and becomes the new accumulated sample value for the pixel when the next frame is processed.

Maximum noise reduction is obtained with a degeneration factor close to unity. However, such a large degeneration factor gives significant smearing the object moves. A degeneration factor of about 0.5 reduces the amplitude of the frame four frames before the current frame to about 10% of its original amplitude. Alternatively, the DSP can measure the difference between the accumulated sample values and the corresponding pixel values of the current frame to determine whether there is motion. The DSP can then determine the degeneration factor according to the amount of motion in the frame. This can be done for the frame as a whole, for regions in the frame, or pixel-by-pixel, as described above in relation to averaging.

Although the application has described illustrative embodiments of the invention in detail, it is to be understood that the invention is not limited to the precise embodiments described, and that various modifications may be practiced within the scope of the invention defined by the appended claims.

I claim:

1. A method of deriving an output video signal from an input video signal generated by an image sensor having an image formed on only a part thereof, the output video signal being derived in response to only a portion of the input video signal generated by the part of the image sensor whereon the image is formed, the input video signal additionally including a portion generated by the part of the image sensor whereon the image is not formed, the method comprising steps of:

providing an image signal generating apparatus wherein the image sensor is mounted, the image signal generating apparatus including a detachable image-forming device selectably attached thereto, the detachable image-forming device including a lens and a proximal fibre-optic bundle, and, when attached to the image signal generating apparatus, forming the image on the part of the image sensor, the image having a size and a position;

receiving a frame of the input video signal from the image sensor, the frame of the input video signal having a structure and including an image portion generated by the part of the image sensor on which the image is formed, and an external portion generated by the part of the image sensor on which the image is not formed;

identifying the image portion of the frame of the input video signal; and extracting from the frame of the input video signal the image portion of the input video signal identified in the identifying step to provide an image portion of a frame the output signal, the frame of the output video signal having a structure substantially similar to the structure of the frame of the input video signal.

2. The method of claim 1, wherein:

in the step of providing an image signal generating apparatus, the detachable image-forming device is of a first type, and the image signal generating apparatus is capable of having a detachable image-forming device of a second type detachably attached thereto in lieu of the detachable image-forming device of the first type, each of the detachable image-forming devices, when attached to the image signal generating apparatus, forming an image on the image sensor, the image having a size and a position depending on the type of the detachable image-forming device, at least one of the detachable image-forming devices forming the image on part of the image sensor;

the method additionally comprises a step of determining the type of the detachable image-forming device forming the image; and the step of identifying the image portion of the frame of the input video signal is performed in response to the type of the detachable image-forming device determined in the determining step.

3. The method of claim 1, wherein:

in the step of providing an image signal generating apparatus, the detachable image-forming device includes storage means for storing image information for the detachable image-forming device, the image information being information whence is identified the image portion of the frame of the input video signal generated by the part of the image sensor whereon the image is formed by the detachable image-forming device;

the method additionally comprises a step of retrieving, from the storage means in the detachable image-forming device, the image information for the detachable image-forming device; and in the step of identifying the image portion of the frame of the input video signal, the image portion of the frame of the input video signal is identified using the image information retrieved from the detachable image-forming device in the retrieving step.

4. The method of claim 1, wherein the method additionally comprises a step of storing, in the detachable image-forming device, image information for the detachable image-forming device, the image information being information whence is identified the image portion of the frame of the input video signal generated by the part of the image sensor whereon the image is formed by the detachable image-forming device; and the step of identifying the image portion of the frame or the input video signal includes a step of retrieving the image information from the detachable image-forming device.

5. The method of claim 1, wherein:

in the step of receiving the frame of the input video signal, the frame of the input video signal includes lines; and the step of identifying the image portion of the frame of the input video signal includes a step of:

analyzing the input video signal to determine ones of the lines of the frame of the input video signal that include an image part generated by the part of the image sensor whereon the image is formed, and an external part generated by the part of the image sensor whereon the image is not formed, and, for each of such lines, finding a position of a boundary between the image part and the external part.

6. The method of claim 1, wherein:

in the step of receiving the frame of the input video signal, the frame of the input video signal includes lines, each of the lines including an image part generated by the part of the image sensor whereon the image is formed, and an external part generated by the part of the image sensor whereon the image is not formed;

in the step of providing an image signal generating apparatus, the image formed on the part of the image sensor has a known shape, an unknown position on the image sensor, and an unknown size; and the step of identifying the image portion of the frame of the input video signal includes steps of:

analyzing the input video signal to determine parameters for calculating the size and the position of the image on the image sensor, and calculating, from the parameters determined in the analyzing step, and from the known shape of the image, the lines including an image portion and an external portion, and, for each of such lines, a position of a boundary between the image part and the external part.

7. The method of claim 2, wherein:

the method additionally comprises a step of storing image information for each type of the detachable image-forming device, the image information being information whence is identified the image portion of the input video signal generated by the part of the image sensor whereon We image is formed by the type of the detachable image-forming device; and the step of identifying the image portion of the frame of the input video signal includes steps of:

retrieving the image information for the type of image-forming device in response to the type of the detachable image-forming device determined in the determining step, and identifying the image portion of the frame of the input video signal using the image information retrieved in the retrieving step.

8. The method of claim 2, wherein:

in the step of providing an image signal generating apparatus, only the detachable image-forming device of the first type forms the image on the part of the image sensor;

the step of determining the type of the detachable image-forming device forming the image on the image sensor is responsive only to the detachable image-forming device of the first type; and the step of identifying the image portion, of the input video signal is performed only when the determining step determines that the detachable image-forming device of the first type is forming the image on the part of the image sensor.

9. The method of claim 3, wherein:

in the step of receiving the frame of the input video signal, the frame of the input video signal includes lines that include an image part generated by the part of the image sensor whereon the image is formed, and an external part generated by the part of the image sensor whereon the image is not formed; and the image information stored in the storage means includes, for each of the lines, a position of a boundary between the image part and the external part of the line.

10. The method of claim 4, wherein:

in the step of receiving the frame of the input video signal, the frame of the input video signal includes lines that include an image part generated by the part of the image sensor whereon the image is formed, and an external part generated by the part of the image sensor whereon the image is not formed; and in the step of storing image information, the image information includes, for each of the lines, a position of a boundary between the image part and the external part of the line.

11. The method of claim 5, wherein, the step of analyzing the input video signal to determine ones of the lines of the frame of the input video signal that include an image part and an external part includes a step of examining each of the lines to detect a boundary between the image part and the external part.

12. The method of claim 6, wherein:

the shape of the image formed on He part of the sensor is substantially circular, and has a radius and a center; and the step of analyzing the input video signal to determine parameters includes a step of determining the radius of the image, and a one of the lines and a position on the one of the lines corresponding to the center of the image as the parameters for calculating the size and the position of the image on the image sensor.

13. The method of claim 6, wherein:

the shape of the image formed on the part of the sensor is substantially elliptical, and has a center and two axes, each of the axes having a length; and the step of analyzing the input video signal to determine parameters includes a step of determining the lengths of the axes, and a one of the lines and a position on the one of the lines corresponding to the center of the image as the parameters for calculating the size and the position of the image on the image sensor.

14. The method of claim 6, wherein the boundary whose position is calculated in the calculating step is a first boundary, and the calculating step additionally calculates, for each of the lines including an image part and an external part, a position of a second boundary between the image part and the external part.

15. The method of claim 7 wherein:

in the step of receiving the frame of the input video signal, the frame of the input video signal includes lines that include an image part generated by the part of the image sensor whereon the image is formed, and an external part generated by the part of the image sensor whereon the image is not formed; and in the step of storing image information the image information includes, for each of the lines, a position of a boundary between the image part and the external part of the line.

16. The method of claim 15, wherein, in the step of storing image information, the image information includes the position of a first boundary between the image part and the external part of each one of the lines, and additionally includes a position of a second boundary between the image part and the external part of the one of the lines.

17. The method of claim 8, wherein:

the step of determining the type of the detachable image-forming device comprises steps of:

providing a switch operable only by the detachable image-forming device of the first type, the switch having a state, and changing the state of the switch to a changed state when the detachable image-forming device of the first type is attached to the image signal generating apparatus; and the step of identifying the image portion of the frame of the input video signal comprises steps of:

retrieving, in response to the changed state of the switch, stored image information for the detachable image-forming device of the first type, the image information being information whence is identified the image portion of the frame of the input video signal generated by the part of the image sensor whereon the image formed by the detachable image-forming device of the first type, and identifying the image portion of the frame of the input video signal using the stored image information retrieved in the retrieving step.

18. The method of claim 9, wherein the image information stored in the storage means includes the position of a first boundary between the image part and the external part of each one of the lines, and additionally includes a position of a second boundary between the image part and the external part of the one of the lines.

19. A method for generating an output video signal from an input video signal, position-dependent luminance errors in the input video signal being corrected in the output video signal, the input video signal being generated by an image sensor having an image formed on only a part thereof, the output video signal being derived in response to only a portion of the input video signal generated by the part of the image sensor whereon the image is formed, the input video signal additionally including a portion generated by the part of the image sensor whereon the image is not formed, the image including an image element having a position in the image, the method comprising steps of:

receiving a frame of the input video signal from the image sensor, the frame of the input video signal having a structure and including an image portion generated by the part of the image sensor on which the image is formed, and an external portion generated by the part of the image sensor on which the image is not formed, the image portion of the input video signal including a signal element corresponding to the image element;

identifying the image portion of the frame of the input video signal;

extracting from the frame of the input video signal the image portion identified in the identifying step;

multiplying the signal element of the image portion by a position-dependent function to provide a modified image portion, the position-dependent function depending on the position in the image of the image element; and incorporating the modified image portion in a frame the output video signal as an image portion thereof, the frame of the output video signal having a structure substantially similar to the structure of the frame of the input video signal.

20. The method of claim 19, wherein:

the image formed on the part of the image sensor is substantially circular, and has a center, and the image element is located in the image at a distance from the center of the image; and in the multiplying step, the position-dependent function depends on the distance of the image element from the center of the image.

21. The method of claim 19, wherein:

the method additionally comprises steps of:
providing an image signal generating apparatus wherein the image sensor is mounted, the image signal generating apparatus including an image-forming device detachably attached thereto, the image-forming device being of a first type, the image signal generating apparatus being capable of having an image-forming device of a second type detachably attached thereto in lieu of the image-forming device of the first type, each of the image-forming devices when attached to the image signal generating apparatus, forming an image on the image sensor, the image having a size and a position depending on the type of the image-forming device, at least one of the image-forming devices forming the image on the part of the image sensor;

determining the type of the image-forming device forming the image on the part of the image sensor to generate image-forming device type information, and retrieving a stored position-dependent function for the type of the image-forming device in response to the image-forming device type information; and in the multiplying step, the signal element is multiplied by the position-dependent function retrieved in the retrieving step for the type of the image forming device.

22. The method of claim 19, wherein:

the method additionally comprises steps of:
providing an image signal generating apparatus wherein the image sensor is mounted, the image signal generating apparatus including an image-forming device detachably attached thereto, the image-forming device being of a first type, the image signal generating apparatus being capable of having an image-forming device of a second type detachably attached thereto in lieu of the image-forming device of the first type, each of the image-forming devices, when attached to the image signal generating apparatus, forming an image on the image sensor, the image having a size and a position depending on the type of the image-forming device, at least one of the image-forming devices forming the image on the part of the image sensor, determining when the image-forming device forming the image on the image sensor is of a type that forms the image on the part of the image sensor, and retrieving a stored position-dependent function for the image-forming device of the type that forms the image on the part of the image sensor; and in the multiplying step, the signal element is multiplied by the position-dependent function retrieved in the retrieving step for the image forming device of the type that forms the image on the part of the image sensor.

23. The method of claim 19, wherein:

the method additionally comprises steps of:
providing an image signal generating apparatus wherein the image sensor is mounted, the image signal generating apparatus including an image-forming device detachably attached thereto, the image-forming device being of a first type, the image signal generating apparatus being capable of having an image-forming device of a second type detachably attached thereto in lieu of the image-forming device of the first type, each of the image-forming devices, when attached to the image signal generating apparatus, forming an image on the image sensor, the image having a size and a position depending on the type of the image-forming device, at least one image-forming device forming the image on the part of the image sensor, and including means for storing a position-dependent function for the image-forming device, and retrieving from the image-forming device forming the image on the image sensor the stored position-dependent function for the image-forming device; and in the multiplying step, the signal element is multiplied by the position-dependent function retrieved in the retrieving step for the image-forming device.

24. The method of claim 19, additionally comprising steps of:

providing an image signal generating apparatus wherein the image sensor is mounted, the image signal generating apparatus including an image-forming device attached thereto, the image-forming device forming the image on the part of the image sensor;

providing a uniformly-illuminated target;

pointing the image-forming device at the uniformly-illuminated target; and executing a set-up procedure to determine a position-dependent function to provide a uniform sensitivity within the image.

25. The method of claim 24, wherein:

the step of executing a set-up routine comprises steps of:

determining a reference luminance for a reference part of the image portion of the input video signal, the reference part of the image portion corresponding to a central region in the image, determining an element luminance for the signal element; and storing a ratio of the reference luminance and the element luminance as the position-dependent function for the signal element; and in the multiplying step, the signal element is multiplied by the stored position-dependent function for the signal element.

26. A method for processing an input video signal generated by an image sensor having an image formed on only a part thereof to generate a control signal for controlling an automatic luminance system responsive to a level of the control signal averaged over a time corresponding to frames of the input video signal, the control signal being generated only in response to a portion of the input video signal generated by the part of the image sensor whereon the image is formed, the input video signal additionally including a portion generated by the part of the image sensor whereon the image is not formed, the method comprising steps of:

receiving a frame of the input video signal from the image sensor, the frame of the input video signal having a structure and including an image portion generated by the part of the image sensor on which the image is formed, and an external portion generated by the part of the image sensor on which the image is not formed, the image portion having an average luminance;

identifying the image portion of the frame of the input video signal; and deriving from the frame of the input video signal a frame of the control signal, the frame of the control signal having an average level corresponding to the average luminance of the image portion of the frame of the input video signal identified in the identifying step.

27. The method of claim 26, wherein the step of deriving a frame of the control signal includes steps of:

extracting from the frame of the input video signal only the image portion identified in the identifying step; and repeatedly inserting the image portion of the frame of the input video signal extracted in the extracting step into the frame of the control signal until the frame of the control signal is filled.

28. The method of claim 26, wherein the step of deriving a frame of the control signal includes steps of:

determining an average luminance of the image portion of the frame of the input video signal identified in the identifying step; and generating the frame of the control signal with a substantially constant level, the substantially constant level corresponding to the average luminance of the image portion of the frame of the input video signal determined in the determining step.

29. The method of claim 26, wherein the image sensor has a first area, and the image formed on the part of the image sensor has a second area, and wherein:

the step of deriving a frame of the control signal includes steps of:

determining the second area in response to the identifying step, calculating a ratio between the first area and the second area, averaging luminance of the frame of the input video signal to generate an average luminance for the frame, and multiplying the average luminance for the frame of the input video signal by the ratio to provide the frame of the control signal.

30. The method of claim 26, additionally providing a reduced sensitivity of the control signal to reflections from small, highly-reflective objects in the image formed on the part of the image sensor, wherein the step of deriving a frame of the control signal includes steps of:

dividing the image portion of the frame of the input video signal identified in the identifying step into parts, each of the parts corresponding to a part of the image formed on the part of the image sensor;

determining an average luminance for each of the parts of the image portion of the frame of the input video signal;

deriving a weighted average luminance from the average luminances of the parts of the image portion, an average luminance substantially greater than other average luminances being included at a reduced weight; and generating the frame of the control signal with a level corresponding to the weighted average luminance.

31. The method of claim 26, additionally providing a reduced sensitivity of the control signal to reflections from small, highly-reflective objects in the image formed on the part of the image sensor, wherein the step of deriving the frame of the control signal includes steps of:

dividing the image portion of the frame of the input video signal identifying in the identifying step into parts, each of the parts corresponding to a part of the image formed on the part of the image sensor;

determining an average luminance for each of the parts of the image portion of the frame of the input video signal;

deriving a weighted average luminance from the average luminances of the parts of the image portion of the input video signal, similar average luminances being included in the weighted average at a greater weight than substantially dissimilar average luminances; and generating the frame of the control signal with a level corresponding to the weighted average luminance.

32. The method of claim 26, wherein the control signal is formatted as a video signal for controlling an automatic luminance system responsive to the average luminance of complete frames of a video signal.

33. The method of claim 29, wherein, in the dividing step, the image portion of the frame of the input video signal identified in the identifying step is divided into parts corresponding to sectors of the image.

34. The method of claim 29, wherein, in the dividing step, the image portion of the frame of the input video signal identified in the identifying step is divided into parts corresponding to radial zones of the image.

35. The method of claim 31, wherein, in the dividing step, the image portion of the frame of the input video signal is divided into parts corresponding to sectors of the image.

36. The method of claim 31, wherein, in the dividing step, the image portion of the frame of the input video signal is divided into parts corresponding to radial zones of the image.

37. A method for deriving an output video signal from an input video signal generated by an image sensor having an image formed on only a part thereof, the output video signal being derived in response to only a portion of the input video signal generated by the part of the image sensor whereon the image is formed, the input video signal additionally including a portion generated by the part of the image sensor whereon the image is not formed, the output video signal having a lower noise level than the portion of the input video signal generated by the part of the image sensor whereon the image is formed, the method comprising steps of:

providing a memory, the memory including pages, each of the pages including storage locations;

receiving a frame of the input video signal from the image sensor, the frame of the input video signal having a structure, being divided into picture elements, and including an image portion generated by the part of the image sensor on which the image is formed, and an external portion generated by the part of the image sensor on which the image is not formed;

identifying the image portion of each frame of the input video signal;

storing the picture elements of the image portion, identified in the identifying step, of successive frames of the input video signal in corresponding ones of the memory locations in successive ones of the pages of the memory;

averaging the picture elements of the image portion of the successive frames of the input video signal stored in the corresponding ones of the memory locations in the successive ones of the pages of the memory to provide average values; and generating an image portion of a frame of the output video signal from the average values provided by the averaging step, the frame of the output video signal having a structure substantially similar to the structure of the frame of the input video signal.

38. The method of claim 37, wherein:

the method additionally comprises a step of determining a movement index between the corresponding picture elements of the successive frames of the image portion of the input video signal stored in the successive ones of the pages of the memory to determine an index for each frame; and the step of averaging the corresponding picture elements of the image portion of the successive frames of the input video signal stored in the corresponding ones of the memory locations is performed only on the frames stored in the ones of the pages of the memory whose index is below a threshold value.

39. The method of claim 38, wherein:

in the determining step, the index is determined from selected parts of the image portion of the input video signal identified in the identifying step; and in the averaging step, the successive ones of the pages of the memory on which averaging is performed on the whole image portion is determined by the index determined for the selected parts of the input video signal in the determining step.

40. The method of claim 38, wherein:

in the determining step, an index for each of the selected parts of the image portion of the input video signal identified in the identifying step is determined; and in the averaging step, the successive one of the pages of the memory on which averaging is performed in each one of the selected parts is determined by the respective index determined for each one of the selected parts of the input video signal in the determining step.

41. A method for deriving an output video signal from an input video signal generated by an image sensor having an image formed on only a part thereof, the output video signal being derived in response to only a portion of the input video signal generated by the part of the image sensor whereon the image is formed, the input video signal additionally including a portion generated by the part of the image sensor whereon the image is not formed, the output video signal having a lower noise level than the portion of the input video signal generated by the part of the image sensor whereon the image is formed, and the method comprising steps of:

receiving a frame of the input video signal from the image sensor, the frame of the input video signal having a structure and including an image portion generated by the part of the image sensor on which the image is formed, and an external portion generated by the part of the image sensor on which the image is not formed, the image portion of the frame of the input video signal being divided into picture elements, each of the picture elements having a sample value;

identifying the image portion of the frame of the input video signal;

providing a memory, the memory including storage locations, each of the storage locations corresponding to one of the picture elements of the image portion of the input video signal;

reading an accumulated sample value for each one of the picture elements of the image portion of the input video signal from a respective one of the storage locations in the memory;

multiplying the accumulated sample value read from the memory in the reading step by a degradation factor to provide a multiplied accumulated sample value;

averaging the multiplied accumulated sample value provided by the multiplying step by the sample value of the one of the picture elements of the frame of the image portion of the input video signal identified in the identifying step to provide an average value, the one of the picture elements corresponding to the multiplied accumulated sample value;

providing the average value provided in the averaging step as a sample value of a picture element of an image portion of the output video signal, the picture element of the image portion of the output video signal corresponding to the one of the picture elements of the input video signal, the frame of the output video signal having a structure substantially similar to the structure of the frame of the input video signal; and storing the average value provided in the averaging step in the one of the storage locations in the memory as the accumulated sample value for the one of the picture elements of the input video signal.

42. The method of claim 41, wherein the step of multiplying the accumulated sample value read from the memory in the reading step by a degradation factor includes steps of:

determining a movement index between the accumulated sample value read from the memory in the reading step and the sample value of the one of the picture elements of the image portion of the input video signal, the one of the picture elements corresponding to the accumulated sample value; and using the movement index to determine the degradation factor.

43. An apparatus for deriving an output video signal from an input video signal generated by an image sensor having an image formed on only a part thereof, the output video signal being derived in response to only a portion of the input video signal generated by the part of the image sensor whereon the image is formed, the input video signal additionally including a portion generated by the part of the image sensor whereon the image is not formed, the apparatus comprising:

an image signal generator wherein the image sensor is mounted, the image signal generator including an image-forming device detachably attached thereto, the image-forming device, when attached to the image signal generator, forming the image on part of the image sensor;

a frame store memory means for storing one of a frame of the input video signal and a frame of the output video signal, the frame of the input video signal having a structure and including an image portion generated by the part of the image sensor on which the image is formed, and an external portion generated by the part of the image sensor on which the image is not formed; and a digital signal processor means, operating together with the frame store memory means, for:
identifying the image portion of the frame of the input video signal in response to identification information; and
extracting only the image portion identified by the identification information from the frame of the input video signal to provide an image portion of the frame of the output video signal, the frame of the output video signal having a structure substantially similar to the structure of the frame of the input video signal.

44. The apparatus of claim 43, wherein:

the digital signal processor means is additionally for receiving the frame of the input video signal; and the digital signal processor means provides the image portion of the frame of the output by:
storing the image portion extracted from the frame of the input video signal in response to the identification information in the frame store memory means,
reading the image portion out of the frame store memory means, and
providing the image portion read out from the frame store memory means as a part of the frame of the output video signal.

45. The apparatus of claim 43, wherein:

the digital signal processor means is additionally for:
receiving the frame of the input video signal, and
storing the frame of the input video signal in the frame store memory means; and the digital signal processor means provides the image portion of the frame of the output by:
reading the image portion out of the frame store memory means in response to the identification information, and
providing the image portion read out of the frame store memory means as a part of the frame of the output video signal.

* * * * *